(12) United States Patent
Schmaier et al.

(10) Patent No.: US 7,074,765 B2
(45) Date of Patent: Jul. 11, 2006

(54) SYNTHETIC PEPTIDE ANALOGS OF ARG-PRO-PRO-GLY-PHE AS SELECTIVE INHIBITORS OF THROMBIN AND THROMBIN ACTIVATION OF PROTEASE ACTIVATED RECEPTORS 1 AND 4

(75) Inventors: Alvin H. Schmaier, Ann Arbor, MI (US); Ahmed A. K. Hasan, Ann Arbor, MI (US)

(73) Assignees: The Regents of the University of Michigan, East Lansing, MI (US); Thromgen, Inc., Ann Arbor, MI (US)

( * ) Notice: Subject to any disclaimer, the term of this patent is extended or adjusted under 35 U.S.C. 154(b) by 206 days.

(21) Appl. No.: 10/426,968

(22) Filed: May 1, 2003

(65) Prior Publication Data

US 2004/0220110 A1    Nov. 4, 2004

(51) Int. Cl.
*A61K 38/08*   (2006.01)
*A61K 39/16*   (2006.01)
*C07K 7/18*    (2006.01)
*C07K 14/00*   (2006.01)

(52) U.S. Cl. .................... 514/12; 514/17; 530/314; 530/324; 530/330

(58) Field of Classification Search .............. 514/12, 514/13, 14, 15, 16, 17; 530/314, 324, 325, 530/326, 327, 328, 329, 330
See application file for complete search history.

(56) References Cited

U.S. PATENT DOCUMENTS

| | | | |
|---|---|---|---|
| 5,681,926 A | 10/1997 | Veber et al. | 530/329 |
| 5,688,768 A | 11/1997 | Coughlin et al. | 514/115 |
| 5,759,994 A | 6/1998 | Coughlin et al. | 514/19 |
| 5,866,681 A | 2/1999 | Scarbborough | 530/326 |
| 5,935,932 A | 8/1999 | Stewart | 514/15 |
| 6,111,075 A | 8/2000 | Xu et al. | 530/350 |
| 6,124,101 A | 9/2000 | Coughlin et al. | 435/7.1 |
| 6,197,541 B1 | 3/2001 | Coughlin et al. | 435/69.1 |
| 6,436,400 B1 | 8/2002 | Xu et al. | 424/143.1 |
| 6,458,923 B1 * | 10/2002 | Kyle | 530/314 |
| 6,515,023 B1 | 2/2003 | Barrow et al. | 514/597 |
| 6,544,750 B1 | 4/2003 | Schmaier | 435/7.1 |
| 6,544,982 B1 | 4/2003 | Selnick et al. | 514/217.1 |
| 6,638,980 B1 | 10/2003 | Su et al. | 514/620 |

OTHER PUBLICATIONS

R. A. Houghten, et al., "Simplified Procedure For Carrying Out Simultaneous Multiple Hydrogen Fluoride Cleavages Of Protected Peptide Resins", Int. J. Peptide Protein Res. 27, 1986, pp. 673-678.

(Continued)

*Primary Examiner*—Jeffrey Edwin Russel
(74) *Attorney, Agent, or Firm*—Venable LLP; Ann S. Hobbs

(57) ABSTRACT

The invention relates to compounds and methods for inhibiting human platelet aggregation, thrombosis and cell activation mediated by PAR1 and PAR4 using peptide analogs of Arg-Pro-Pro-Gly-Phe that contain one or more amino acid substitutions. The invention also includes screening methods for identifying compounds that inhibit thrombin mediated activities.

18 Claims, 14 Drawing Sheets

OTHER PUBLICATIONS

R.B. Merrifield, "Solid Phase Peptide Synthesis. I. The Synthesis Of A Tetrapeptide", Synthesis Of A Tetrapeptide, Jul. 20, 1963, vol. 85, pp. 2149-2154.

S. K. Fisher, et al., "Muscarinic Receptor Regulation Of Cytoplasmic $Ca^{2+}$ Concentrations In Human SK-N-SH Neuroblastoma Cells: $Ca^{2+}$ Requirements For Phospholipase C Activation", Neuroscience Laboratory and Department of Pharmacology, University of Michigan, Ann Arbor, Michigan, Molecular Pharmacology, vol. 35, pp. 195-204 (1989).

U. B. Rasmussen, et al., "A Peptide Ligand Of the Human Thrombin Receptor Antagonizes α-Thrombin And Partially Activates Platelets", The Journal of Biological Chemistry, vol. 268, No. 19. Jul. 5, 1993, pp. 14322-14328.

G. Salvesen, et al., "Human Low-$M_r$ Kininogen Contains Three Copies Of A Cystatin Sequence That Are Divergent In Structure And In Inhibitory Activity For Cysteine Proteinases", Biochem. J. (1986) 234, 429-434.

R.A.Houghten, "General Method for the Rapid Solid-Phase Synthesis of Large Numbers of Peptides: Specificity of Antigen-Antibody Interaction at the Level of Individual Amino Acids" Proc. Natl. Acad. Sci. USA, vol. 82, pp. 5131-5135, Aug. 1985.

W. XU, et al. "Cloning And Characterization Of Human Protease-Activated Receptor 4", Proc. Natl. Acad. Sci. USA, vol. 95., pp. 6642-6646, Jun. 1998.

J. Kellermann, et al. "Completion Of The Primary Structure Of Human High-Molecular-Mass Kininogen, The amino acid sequence of the entire heavy chain and evidence for its evolution by gene triplication", Eur. J. Biochem. 154, 471-478 (1986).

L.F. Brass, et al. "Structure And Function Of The Human Platelet Thrombin Receptor" The Journal Of Biological Chemistry, vol. 267, No. 20, Jul. 15, 1992, pp. 13795-13798.

T.H. Vu, et al. "Molecular Cloning Of A Functional Thrombin Receptor Reveals A Novel Proteolytic Mechanism Of Receptor Activation", Cell, vol. 64, pp. 1057-1068, 1991.

N. Kitamura, et al., "Structural Organization Of The Human Kininogen Gene And A model For Its Evolution" The Journal of Biological Chemistry, vol. 260, No. 15, pp. 8610-8617, Jul. 15, 1985.

Y. Takagaki, et al., "Cloning And Sequence Analysis Of eDNAs For Human High Molecular Weight And Low Molecular Weight Prekininogens", The Journal of Biological Chemistry, vol. 260, No. 14, Jul. 15, 1985, pp. 8601-8609.

M.A. Tayeh, et al., "Surface-Induced Alterations In the Kinetic Pathway For Cleavage Of Human High Molecular Weight Kininogen By Plasma Kallikrein", The Journal of Biological Chemistry, vol. 269, No. 23, Jun. 10, 1994, pp. 16318-16325.

A.A.K. Hasan, MD. Ph.D. et al., "Bradykinin And Its Metabolite, Arg-Pro-Pro-Gly-Phe, Are Seletive Inhibitors of α-Thrombin-Induced Platelet Activation", Circulation, vol. 94, No. 3, Aug. 1, 1996, pp. 517-528.

W.D. Ehringer, et al., "Bradykinin Antagonizes The Effects Of α-Thrombin", Inflammation, vol. 21, No. 3, pp. 279-298, 1997.

M.R. E Silva, et al., "Bradykinin, A Hypotensive And Smooth Muscle Stimulating Factor Released From Plasma Globulin By Snake Venoms And By Trypsin", Amer. J. Physiol., vol. 156. pp. 261-273, 1949.

F.J. Meloni, et al., "Low Molecular Weight Kininogen Binds To Platelets to Modulate Thrombin-Induced Platelet Activation", The Journal of Biological Chemistry, vol. 266, No. 11, Apr. 15, 1991, pp. 6786-6794.

Y. Jiang, et al., "Domain 3 Of Kininogens Contains A Cell-Binding Site And A Site That Modifies Thrombin Activation Of Platelets", The Journal of Biological Chemistry, vol. 267, No. 6, Feb. 25, 1992, pp. 3712-3717.

A.A.K. Hasan, et al., "Thrombostatin Inhibits Induced Canine Coronary Thrombosis", Thromb Haemost 1999, vol. 82, pp. 1182-1187.

D.B. Cleary, et al., "Establishing The Inhibitory Effects Of Bradykinin On Thrombin", Archives Of Biochemistry and Biophysics 410, (2003), pp. 96-106.

A.A.K. Hasan, et al., "Thrombostatin Inhibits Cyclic Flow Variations In Stenosed Canine Coronary Arteries", Thromb Haemost, 2001, vol. 86, pp. 1296-1304.

Y.M. Ayala, et al., "Molecular Mapping Of Thrombin-Receptor Interactions", Proteins: Structure, Function and Genetics, vol. 45, 2001, pp. 107-116.

A.R. Prieto, et al., "Thrombostatin, A Bradykinin Metabolite, Reduces Platelet Activation In A Model Of Arterial Wall Injury", Cardiovascular Research 53, (2002) 984-992.

B.F. Santos, et al., "Interaction Of Viper Venom Serine Peptidases With Thrombin Receptors On Human Platelets", FEBS Letters, 477, (2000) pp. 199-202.

C.H. Chay, et al., "A Functional Thrombin Receptor (Par 1) Is Expressed On Bone-Derived Prostate Cancer Cell Lines", Urology, vol. 60, 2002, pp. 760-765.

Y. Jiang, et al., "Thrombin-Receptor Activation And Thrombin-Induced Brain Tolerance", Journal of Cerebral Blood Flow & Metabolism, vol. 22, pp. 404-410 (2002).

A.AK. Hasan, et al., "Mechanisms Of Arg-Pro-Pro-Gly-Phe Inhibition Of Thrombin", Am J Physiol Heart Circ Physiol, vol. 285, 2003, pp. H183-193.

Srikanth et al. "Reduced Rate of Bradykinin Metabolism Protects the Mouse from Thrombosis" *Blood.* 100, 24a (2002).

Hasan et al., "The Mechanism of Thrombostatin Inhibition of Thrombin", *Blood.* 98, 530a, (2001).

Altrogge et al. An Assay for High-Sensitivity Detection of Thrombin Activity and Determination of Proteases Activating or Inactivating Protease-Activated Receptors. Analytical Biochemistry. 2000, vol. 277, pp. 33-45.

Dendorfer et al. Structural requirements for B2-agonists with improved degradation stability. Immunopharmacology. 1999, vol. 45, pp. 199-205.

Reissmann et al. Structure activity relationships for bradykinin antagonists on the inhibition of cytokine release and the release of histamine. Peptides. 2000, vol. 21, pp. 527-533.

\* cited by examiner

SEQUENCE LISTING

```
<160> NUMBER OF SEQ ID NOS: 31

<210> SEQ ID NO 1
<211> LENGTH: 9
<212> TYPE: PRT
<213> ORGANISM: Unknown Organism
<220> FEATURE:
<223> OTHER INFORMATION: Description of Unknown Organism: Bradykinin
      peptide

<400> SEQUENCE: 1

Arg Pro Pro Gly Phe Ser Pro Phe Arg
  1               5

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 2

Ser Phe Leu Leu Arg Asn
 1               5

<210> SEQ ID NO 3
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Asn Ala Thr Leu Asp Pro Arg Ser Phe Leu Leu Arg
 1               5                  10

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Arg Pro Pro Gly Phe
 1               5

<210> SEQ ID NO 5
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Arg Pro Pro Gly
 1

<210> SEQ ID NO 6
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Asp Lys Tyr Glu Pro Phe Trp Glu Asp Glu Glu Lys
 1               5                  10

<210> SEQ ID NO 7
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Trp Glu Phe Tyr
 1

<210> SEQ ID NO 8
<211> LENGTH: 5
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 8

Leu Pro Ala Pro Arg
 1               5

<210> SEQ ID NO 9
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ser Ile Leu Pro Ala Pro Arg Gly Tyr Pro Gly Gln
 1               5                  10

<210> SEQ ID NO 10
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Arg Pro Pro Gly Cys
 1               5

<210> SEQ ID NO 11
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Phe Pro Arg Pro Gly
 1               5

<210> SEQ ID NO 12
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: UNSURE
<222> LOCATION: (1)..(5)
<223> OTHER INFORMATION: Residues 1-5 are independently one of 20
      natural amino acids

<400> SEQUENCE: 12

Xaa Xaa Xaa Xaa Xaa
 1               5

<210> SEQ ID NO 13
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (5)
<223> OTHER INFORMATION: Phe-biotin

<400> SEQUENCE: 13

Arg Pro Pro Gly Phe
 1               5

<210> SEQ ID NO 14
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)
<223> OTHER INFORMATION: Gln-biotin

<400> SEQUENCE: 14

Ser Ile Leu Pro Ala Pro Arg Gly Tyr Pro Gly Gln
 1               5                  10

<210> SEQ ID NO 15
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Pro Arg Ser Phe
 1

<210> SEQ ID NO 16
<211> LENGTH: 74
<212> TYPE: PRT
<213> ORGANISM: Homo sapiens

<400> SEQUENCE: 16

Ala Arg Arg Pro Glu Ser Lys Ala Thr Asn Ala Thr Leu Asp Pro Arg
 1               5                  10                  15

Ser Phe Leu Leu Arg Asn Pro Asn Asp Lys Tyr Glu Pro Phe Trp Glu
                20                  25                  30

Asp Glu Glu Lys Asn Glu Ser Gly Leu Thr Glu Tyr Arg Leu Val Ser
            35                  40                  45

Ile Asn Lys Ser Ser Pro Leu Gln Lys Gln Leu Pro Ala Phe Ile Ser
        50                  55                  60

Glu Asp Ala Ser Gly Tyr Leu Thr Ser Ser
 65                  70

<210> SEQ ID NO 17
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gcaacaaatg ccacctcatt tcttctcagg                                        30
```

<210> SEQ ID NO 18
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
aatgccacct tagatcttct caggaacccc                                    30

<210> SEQ ID NO 19
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19 accccccaatg ataaagagga tgaggagaaa aatg                              34

<210> SEQ ID NO 20
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Leu Asp Pro Arg
  1

<210> SEQ ID NO 21
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Phe Pro Arg Pro Gly
  1               5

<210> SEQ ID NO 22
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
gaattccata tgggcggcac ccagaccccc agcgtc                             36

<210> SEQ ID NO 23
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
ccgctcgagt cacctggtgg gcacccagcc cagaag                             36

-continued

```
<210> SEQ ID NO 24
<211> LENGTH: 61
<212> TYPE: PRT
<213> ORGANISM: Homo sapiens

<400> SEQUENCE: 24

Gly Gly Thr Gln Thr Pro Ser Val Tyr Asp Glu Ser Gly Ser Thr Gly
 1               5                  10                  15

Gly Gly Asp Asp Ser Thr Pro Ser Ile Leu Pro Ala Pro Arg Gly Trp
            20                  25                  30

Pro Gly Gln Val Cys Ala Asn Asp Ser Asp Thr Leu Glu Leu Pro Asp
        35                  40                  45

Ser Ser Arg Ala Leu Leu Leu Gly Trp Val Pro Thr Arg
    50                  55                  60

<210> SEQ ID NO 25
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: beta-Ala

<400> SEQUENCE: 25

Ala Lys Lys Lys Arg Pro Pro Gly Phe Arg Pro Pro Gly Phe Arg Pro
 1               5                  10                  15

Pro Gly Phe Arg Pro Pro Gly Phe
            20

<210> SEQ ID NO 26
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: beta-Ala
<220> FEATURE:
<221> NAME/KEY: MOD_RES
<222> LOCATION: (5)
<223> OTHER INFORMATION: D-Arg or Arg
<220> FEATURE:
<221> NAME/KEY: MOD_RES
<222> LOCATION: (6)..(7)
<223> OTHER INFORMATION: Oic, Hyp, Idg, Pro, Tic, F5F, or Thi
<220> FEATURE:
<221> NAME/KEY: MOD_RES
<222> LOCATION: (9)
<223> OTHER INFORMATION: Phe, Oic, Hyp, Idg, Tic, F5F or Thi
<220> FEATURE:
<221> NAME/KEY: MOD_RES
<222> LOCATION: (10)
<223> OTHER INFORMATION: D-Arg or Arg
<220> FEATURE:
<221> NAME/KEY: MOD_RES
<222> LOCATION: (11)..(12)
<223> OTHER INFORMATION: Oic, Hyp, Idg, Pro, Tic, F5F, or Thi
<220> FEATURE:
<221> NAME/KEY: MOD_RES
<222> LOCATION: (14)
<223> OTHER INFORMATION: Phe, Oic, Hyp, Idg, Tic, F5F or Thi
<220> FEATURE:
<221> NAME/KEY: MOD_RES
```

```
<222> LOCATION: (15)
<223> OTHER INFORMATION: D-Arg or Arg
<220> FEATURE:
<221> NAME/KEY: MOD_RES
<222> LOCATION: (16)..(17)
<223> OTHER INFORMATION: Oic, Hyp, Idg, Pro, Tic, F5F, or Thi
<220> FEATURE:
<221> NAME/KEY: MOD_RES
<222> LOCATION: (19)
<223> OTHER INFORMATION: Phe, Oic, Hyp, Idg, Tic, F5F or Thi
<220> FEATURE:
<221> NAME/KEY: MOD_RES
<222> LOCATION: (20)
<223> OTHER INFORMATION: D-Arg or Arg
<220> FEATURE:
<221> NAME/KEY: MOD_RES
<222> LOCATION: (21)..(22)
<223> OTHER INFORMATION: Oic, Hyp, Idg, Pro, Tic, F5F, or Thi
<220> FEATURE:
<221> NAME/KEY: MOD_RES
<222> LOCATION: (24)
<223> OTHER INFORMATION: Phe, Oic, Hyp, Idg, Tic, F5F or Thi

<400> SEQUENCE: 26

Ala Lys Lys Lys Xaa Xaa Xaa Gly Xaa Xaa Xaa Xaa Gly Xaa Xaa Xaa
 1               5                  10                  15

Xaa Gly Xaa Xaa Xaa Xaa Gly Xaa
            20

<210> SEQ ID NO 27
<211> LENGTH: 15
<212> TYPE: PRT
<213> ORGANISM: Artificial Sequence
<220> FEATURE:
<223> OTHER INFORMATION: Description of Artificial Sequence: Synthetic
      fusion construct

<400> SEQUENCE: 27

His His His His His His His His His His Asp Asp Asp Asp Lys
 1               5                  10                  15

<210> SEQ ID NO 28
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Oic

<400> SEQUENCE: 28

Arg Xaa Pro Gly Phe
 1               5

<210> SEQ ID NO 29
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Oic

<400> SEQUENCE: 29

Arg Pro Xaa Gly Phe
```

-continued

```
<210> SEQ ID NO 30
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Hyp

<400> SEQUENCE: 30

Arg Pro Xaa Gly Phe
  1               5

<210> SEQ ID NO 31
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Hyp

<400> SEQUENCE: 31

Arg Xaa Pro Gly Phe
  1               5
```

SYNTHETIC PEPTIDE ANALOGS OF ARG-PRO-PRO-GLY-PHE AS SELECTIVE INHIBITORS OF THROMBIN AND THROMBIN ACTIVATION OF PROTEASE ACTIVATED RECEPTORS 1 AND 4

REFERENCE TO GOVERNMENT GRANT

The invention described herein was made, in part, in the course of work supported by the National Heart Lung and Blood Institute under Grant Nos. HL56415, HL61081 and HL61981 and the Michigan Life Science Corridor Proposal #1607. The United States Government has certain rights in the invention.

FIELD OF INVENTION

This invention relates to the inhibition of α- and γ-thrombin-induced platelet and cell activation.

BACKGROUND OF THE INVENTION

Bradykinin (Arg-Pro-Pro-Gly-Phe-Ser-Pro-Phe-Arg, SEQ ID NO:1) is a vasoactive peptide released from the precursor plasma kininogens by plasma and tissue kallikreins and other enzymes (Silva et al., *Amer. J. Physiol.* 156: 261–274 (1949)). The parent proteins of bradykinin, high (HK) and low (LK) molecular weight kininogens were recognized to have the ability to inhibit α- and γ-thrombin-induced platelet activation (Meloni et al., *J. Biol. Chem.* 266, 6786 (1991); Puri et al., *Blood* 77, 500 (1991)). Both low and high molecular weight kininogens have identical amino acid sequences from their amino-terminus through 12 amino acids beyond the carboxy-terminus of bradykinin. Both LK and HK share a common heavy chain (62 kDa), the bradykinin (BK) moiety (0.9 kDa), and the first 12 amino acids of the amino terminal portion of each of their "light chains" (Takagaki et al., *J. Biol. Chem.* 260, 8601–8609 (1985); Kitamura et al., *J. Biol. Chem.*, 260, 8610–8617 (1985)). This identity corresponds to residues 1 through about residue 383. See Salveson et al., *Biochem J.* 243, 429 (1986); Kellerman et al., *Eur. J. Biochem.* 154, 471 (1986). The HK and LK kininogens diverge in the size of their light chains; the light chain of LK is 4 kDa; that of HK is 56 kDa. (Takagaki et al., supra; Kitamura et al., supra.). The kininogens prevent thrombin-induced platelet activation. Full-length kininogens prevent thrombin from binding to platelets. They do not interfere with thrombin's ability to proteolyze, i.e. cleave fibrinogen, which allows released fibrin monomer to make a fibrin clot. Thus, the prior art indicated that kininogens' ability to inhibit thrombin activation of platelets was not due to their direct interaction with the thrombin molecule itself (Meloni et al., supra; Puri et al., supra).

The thrombin inhibitory activity of the kininogens was thought to be localized to an isolated domain 3 of the kininogens' heavy chain, because domain 3 retained all the thrombin inhibitory activity of the whole protein (Jiang et al., *J. Biol. Chem.* 267, 3712 (1992)). The thrombin inhibitory activity of the kininogens was later found to be associated with domain 4, the bradykinin sequence, which was attached to the carboxyterminal end of isolated domain 3 prepared by proteolytic cleavage of whole LK (Hasan et al., *Circulation* 94, 517–528 (1996); Tayeh et al., *J. Biol. Chem.* 269, 16318–16325 (1994)). Bradykinin, itself, has been recognized to antagonize the effects of α-thrombin (Ehringer et al., *Inflammation.* 21:279–298 (1997)). The thrombin inhibitory region of domain 4, the bradykinin sequence, demonstrated a number of features. This sequence did not prevent thrombin from binding to platelets and it did not prevent the thrombin receptor activation peptide (TRAP), SFLLRN (Ser-Phe-Leu-Leu-Arg-Asn, SEQ ID NO:2), from stimulating calcium mobilization and platelet aggregation in platelets. This sequence from domain 4 prevented thrombin-activated platelets from losing an epitope to monoclonal antibody SPAN12. Monoclonal antibody SPAN12 is directed to the thrombin cleavage site on protease activated receptor 1 (PAR1) (Hasan et al., supra; Vu et al., *Cell* 64, 1057–1068 (1991); Brass et al., *J. Biol. Chem.* 267, 13795–13798 (1992)). Monoclonal antibody SPAN12 was raised to the peptide NATLDPRSFLLR (Asn-Ala-Thr-Leu-Asp-Pro-Arg-Ser-Phe-Leu-Leu-Arg, SEQ ID NO:3) (Brass et. al., supra.). Further, bradykinin analog peptides prevented α-thrombin from cleaving the peptide NATLDPRSFLLR (SEQ ID NO:3) between arginine and serine, the identical place on PAR1 that thrombin cleaves to activate this receptor. Although there are a number of peptide analogs of bradykinin that demonstrated thrombin inhibiting activity against platelet activation, the minimal sequences retaining this activity are the peptides, RPPGF (Arg-Pro-Pro-Gly-Phe, SEQ ID NO:4), RPPG (Arg-Pro-Pro-Gly, SEQ ID NO:5), and RPP (Arg-Pro-Pro). FITC-labeled (fluorescein isothiocyanate) RPPGF (SEQ ID NO:4) has the ability to directly bind to platelets (Hasan et al., *Thromb Haemost.* 82, 1182–1187 (1999)). These data indicated that the RPPGF (SEQ ID NO:4) and related bradykinin analog peptides have the ability to bind to platelets to prevent thrombin-induced platelet activation. RPPGF (SEQ ID NO:4) and its related peptide, MAP4-RPPGF (β-Ala-Lys-2Lys-4(Arg-Pro-Pro-Gly-Phe)) have the ability to interfere with α- or γ-thrombin-induced platelet activation two ways: at high concentrations these peptides are retrobinders to the active site of thrombin ($K_i$=1.75 mM). At lower concentrations they bind to protease activated receptor 1 (PAR1) near the thrombin cleavage site to prevent thrombin cleavage of the extracellular domain of PAR1 (Hasan et al., *Blood.* 98, 530a, (2001); Hasan et al. *Amer J Physiol. Heart Circ Physiol.* In Press, (2003)). Bradykinin, itself, has been shown to be a direct inhibitor of thrombin with a $K_i$ between 170 to 326 μM (Cleary et al., *Arch. Biochem. Biophys.* 410, 96–106 (2003)). Last, thrombin has two binding sites on PAR1. It binds by its exosite I region to a hirugen-like region on the carboxy-terminus of the extracellular fragment of PAR1 which includes the amino acid sequence Asp-Lys-Tyr-Glu-Pro-Phe-Trp-Glu-Asp-Glu-Glu-Lys (SEQ ID NO:6) (Ayala et al. *Proteins:Structure, Function, and Genetics.* 45, 107–116 (2001)). It also binds to a region adjacent to the thrombin cleavage site on PAR1, the sequence Leu-Asp-Pro-Arg (SEQ ID NO:7) (Ayala et al. *Proteins:Structure, Function, and Genetics.* 45, 107–116 (2001)). Alternatively, when thrombin cleaves PAR4, it only binds to a region adjacent to the thrombin cleavage site Leu-Pro-Ala-Pro-Arg (SEQ ID NO:8) (Ayala et al. *Proteins:Structure, Function, and Genet-* ics. 45, 107–116 (2001)). On human PAR4, there is no equivalent hirugen binding region as seen on PAR1 on the extracellular fragment of PAR4.

The importance of the use of RPPGF (SEQ ID NO:4) and related compounds has been shown in animals studies. RPPGF (SEQ ID NO:4) prevents coronary thrombosis in the canine electrolytic injury model similar to aspirin treatment (Hasan et al. *Thrombosis and Haemostasis* 82, 1182–1187 (1999)). MAP4-RPPGF (β-Ala-Lys-2Lys-4(Arg-Pro-Pro-Gly-Phe)) prevents cyclic flow variations in the Folt's model for canine coronary thrombosis to a similar degree as aspirin or clopidogrel (Hasan et al. *Thrombosis and Haemostasis* 86, 1296–1304 (2001)). RPPGF (SEQ ID NO:4) infusion delays the time to death in lipopolysaccharide-treated rats (Morinelli et al. *J. Pharm Exp. Ther.* 296, 71–76 (2001)). RPPGF (SEQ ID NO:4) reduced platelet activation and deposition in an ex vivo model of balloon injury to the vessel wall similar to the effects of aspirin (Prieto et al. *Cardiovascular Research*. 53, 984–992 (2001)). Last, MAP4-RPPGF delays the time to thrombosis of the mouse carotid artery and inhibits mouse platelet aggregation (Srikanth et al. *Blood*. 100, 24a, (2002))

The present invention relates to inhibition of thrombin-induced activation in human cells. Inhibition of thrombin activation of platelets can be either through an inhibitor of thrombin directed to the thrombin molecule itself or an inhibitor directed to substrates of thrombin. PAR1 and protease activated receptor 4 (PAR4) (Xu et al. *Proc. Natl. Acad. Sci*. 95, 6642, (1998) are specific substrates of thrombin to which this class of inhibitors are directed. The present invention is directed to inhibition of these thrombin substrates on any cell that expresses PAR1 or PAR4. These cells include normal platelets, endothelial cells, smooth muscle cells, fibroblasts, neuronal cells, or any other normal or cancerous cell that contains these receptors. The present invention does not address inhibition of ADP-induced platelet activation as related to the thienopyridines class of agents, ticlopidine and clopidogrel, which are directed to the platelet receptor $P2Y_{12}$. Similarly, the present invention does not address inhibition of platelet aggregation by the formation of the heterodimeric complex of platelet glycoprotein IIb/IIIa (i.e. integrin $\alpha_{IIb}\beta_3$). These compounds include the human-mouse chimeric monoclonal antibody 7E3c (ReoPro®, abciximab), eptifibatide (Integrilin™), and tirofiban (Aggrastat®). This invention does not address aspirin inhibition of platelet activation by inhibition of platelet cyclooxygenase. Further these compounds do not address activation of the platelet thromboxane receptor by U46619. Nor do these studies address activation of the collagen receptors $\alpha_2\beta_1$ integrin or GPVI/FcγII. Last, these investigations have nothing to do with activation of glycoprotein Ib/IX/V complex on the platelet surface.

The following abbreviations have been used:

| | |
|---|---|
| A: | any naturally occurring amino acid or a synthetic amino acid as shown in Table V |
| BK: | bradykinin (Arg-Pro-Pro-Gly-Phe-Ser-Pro-Phe-Arg, SEQ ID NO:1); |
| D3: | domain 3 of kininogens; |
| D4: | domain 4 of kininogen that is the bradykinin region; |
| FITC: | fluorescein isothiocyanate; |
| HK: | high molecular weight kininogen; |
| LK: | low molecular weight kininogen; |
| MAP4- RPPGF: | A four-branched peptide consisting of a β-alanine core with a single lysine attached at its amino terminal end followed by two additional lysines. Each lysine will then have two RPPGF (SEQ ID NO:4) peptides attached by the phenylalanine to each of the lysines; |
| NAT12: | peptide sequence Asn-Ala-Thr-Leu-Asp-Pro-Arg-Ser-Phe-Leu-Leu-Arg (SEQ ID NO:3) that spans the α-thrombin cleavage site on the thrombin receptor; |
| SIL 12 | peptide sequence Ser-Ile-Leu-Pro-Ala-Pro-Arg-Gly-Tyr-Pro-Gly-Gln (SEQ ID NO:9) that spans the α- and γ-thrombin cleavage site on the thrombin receptor. |
| PAR1: | protease activated receptor 1; |
| PAR4 | protease activated receptor 4; |
| PTCA: | percutaneous transluminal coronary angioplasty; |
| RPPGF: | Arg-Pro-Pro-Gly-Phe (SEQ ID NO:4); |
| RPPGC: | Arg-Pro-Pro-Gly-Cys (SEQ ID NO:10) |
| RPPG: | Arg-Pro-Pro-Gly (SEQ ID NO:5); |
| RPP: | Arg-Pro-Pro; |
| FPRPG: | Phe-Pro-Arg-Pro-Gly (SEQ ID NO:11) |
| SPAN12: | a monoclonal antibody specific for the sequence Asn-Ala-Thr-Leu-Asp-Pro-Arg-Ser-Phe-Leu-Leu-Arg (SEQ ID NO:3) that spans the α-thrombin cleavage site on the thrombin receptor; and |
| X: | nomenclature for one of nine synthetic amino acids |
| Z: | nomenclature for any naturally occurring amino acid. |
| APTT | activated partial thromboplastin time, an assay to measure the clotting of plasma. |
| PT | prothrombin time, an assay to measure the clotting of plasma |
| TCT | thrombin clotting time, an assay to measure the integrity of fibrinogen in plasma or with purified fibrinogen |

SUMMARY OF THE INVENTION

The invention relates to a series of compounds to inhibit thrombin-induced platelet or human cell activation upon administering an effective amount of a peptide that inhibits thrombin activation of platelets or human cells, wherein said peptide comprises an amino acid sequence of the formula:

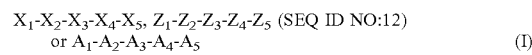

$$X_1\text{-}X_2\text{-}X_3\text{-}X_4\text{-}X_5, Z_1\text{-}Z_2\text{-}Z_3\text{-}Z_4\text{-}Z_5 \text{ (SEQ ID NO:12)}$$
$$\text{or } A_1\text{-}A_2\text{-}A_3\text{-}A_4\text{-}A_5 \quad (I)$$

wherein:
each of $X_{1-5}$ is independently one of 9 synthetic amino acid residues, each of $Z_{1-5}$ is independently one of 20 natural amino acid residues set forth in TABLES IV or V below, and each of $A_{1-5}$ is independently either a synthetic or natural amino acid residue from Table IV or V.

In a preferred embodiment, the peptide comprises a peptide compound $A_{1-5}$ wherein:

$A_1$ is selected from the group consisting of D-arginine (r) and L-arginine (R);

$A_2$ is selected from the group consisting of (2S, 3aS, 7aS)-octahydroindole-2-carboxlic acid (Oic), 4-Hydroxyproline (Hyp), α-(2-indanyl)glycine (Idg), proline (P), 1,2,3,4-tetrahydroisoquinoline-3-carboxylic acid (Tic), Pentafluorophenylalanine (F5F) and β-(2-thienyl)-L-alanine (Thi);

$A_3$ is selected from the group consisting of Oic, Hyp, Idg, P, Tic, F5F, and Thi;

$A_4$ is glycine (G);

$A_5$ is selected from the group consisting of L-phenylalanine (F), Oic, Hyp, Idg, Tic, F5F and Thi;

and wherein said compound contains 28 or fewer, more preferably 10 or fewer, amino acid residues. In more preferred embodiments, one or two substitutions are made to parent compound RPPGF. In a particularly preferred embodiment, $A_1$ is D-Arg. The invention preferably includes at least one non-naturally-occurring amino acid residue.

The invention also relates to a series of compounds to inhibit thrombin-induced platelet or human cell activation upon administering an effective amount of a peptide that inhibits thrombin activation of platelets or human cells, wherein said peptide has an amino acid sequence of the formula:

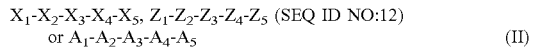

wherein:
each of $X_{1-5}$ is independently one of 9 synthetic amino acid residues, each of $Z_{1-5}$ is independently one of 20 natural amino acid residues set forth in TABLES IV or V below, and each of $A_{1-5}$ is independently either a synthetic or natural amino acid residue from Table IV or V.

In a preferred embodiment, the peptide comprises a peptide compound $A_{1-5}$ wherein:

$A_1$ is selected from the group consisting of D-arginine (r) and L-arginine (R);

$A_2$ is selected from the group consisting of (2S, 3aS, 7aS)-octahydroindole-2-carboxlic acid (Oic), Hydroxyproline (Hyp), α-(2-indanyl)glycine (Idg), proline (P), 1,2,3,4-tetrahydroisoquinoline-3-carboxylic acid (Tic), Pentafluorophenylalanine (F5F) and β-(2-thienyl)-L-alanine (Thi);

$A_3$ is selected from the group consisting of Oic, Hyp, Idg, P, Tic, F5F, and Thi;

$A_4$ is glycine (G);

$A_5$ is selected from the group consisting of L-phenylalanine (F), Oic, Hyp, Idg, Tic, F5F and Thi;

and wherein said compound comprises 28 or fewer, preferably 10 or fewer, amino acid residues. The compound preferably includes at least one non-naturally-occurring amino acid residue. In more preferred embodiments, one or two substitutions are made to parent compound RPPGF. In a particularly preferred embodiment, $A_1$ is L-Arg.

The invention further relates to a series of compounds to inhibit thrombin-induced platelet or human cell activation upon administering an effective amount of a peptide that inhibits thrombin activation of platelets or human cells, wherein said peptide comprises an amino acid sequence of the formula:

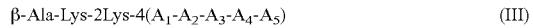

wherein each of $A_{1-5}$ is independently either a synthetic or natural amino acid residue from Table IV or V. In preferred embodiments, $A_1$ is selected from the group consisting of D-arginine (r) and L-arginine (R);

$A_2$ is selected from the group consisting of (2S, 3aS, 7aS)-octahydroindole-2-carboxlic acid (Oic), Hydroxyproline (Hyp), α-(2-indanyl)glycine (Idg), proline (P), 1,2,3,4-tetrahydroisoquinoline-3-carboxylic acid (Tic), Pentafluorophenylalanine (F5F) and β-(2-thienyl)-L-alanine (Thi);

$A_3$ is selected from the group consisting of Oic, Hyp, Idg, P, Tic, F5F, and Thi;

$A_4$ is glycine (G);

$A_5$ is selected from the group consisting of L-phenylalanine (F), Qic, Hyp, Idg, Tic, F5F and Thi.

In more preferred embodiments, one or two substitutions are made to parent compound RPPGF (SEQ ID NO:4). In a particularly preferred embodiment, $A_1$ is D-Arg. Preferably the compound includes at least one non-naturally-occurring amino acid residue.

In one embodiment, the invention comprises treating platelets or human cells with a compound of Formula I or Formula II to inhibit thrombin activation of platelets or activation of other cells, which express the thrombin receptors PAR1 or PAR4. Some of the preferred analogs include rOicPGF (D-Arg-Oic-Pro-Gly-Phe), rOicPGIdg (D-Arg-Oic-Pro-Gly-Idg), rOicHypGThi (D-Arg-Oic-Hyp-Gly-Thi), rOicHypGIdg (D-Arg-Oic-Hyp-Gly-Idg), rOicPGThi (D-Arg-Oic-Pro-Gly-Thi), rOicOicGIdg (D-Arg-Oic-Oic-Gly-Idg), rOicOicGThi (D-Arg-Oic-Oic-Gly-Thi), rIdgTicGF (D-Arg-Idg-Tic-Gly-Phe), rOicOicGF (D-Arg-Oic-Oic-Gly-Phe), rOicHypGF (D-Arg-Oic-Hyp-Gly-Phe).

In another embodiment, the invention comprises treating platelets or human cells with a compound of Formula III to inhibit thrombin activation of platelets or activation of other cells that express the thrombin receptor. Preferred analogs of this embodiment include MAP4-rOicPGF (□-Ala-Lys-2Lys-4(D-Arg-Oic-Pro-Gly-Phe)).

MAP4-rOicPGF is a multiantigenic peptide consisting of a Lys-β-alanine core with two lysines attached to the 2 free amino groups on the first lysine and four molecules of rOicPGF attached to the two free amino groups on the second lysine.

An object of administration of these peptides of Formulae I, II, or III to cells is to prevent thrombosis, i.e., an occlusion of a vessel due to formation of a platelet-rich, fibrin-rich or a mixed platelet-fibrin thrombus. Accordingly, the invention relates to the foregoing analogs, and to the contact of these analogs with platelets and human cells which express the thrombin receptor to prevent thrombosis. Another object of this invention is to inhibit cancer cell growth, invasion, or metastasis where the thrombin receptors PAR and/or PAR4 are expressed. Further, this invention could be used to prevent brain edema due to the presence of thrombin.

Included in the invention are methods of inhibiting thrombin-mediated activities comprising administration of the compounds of Formulae I, II and III to cells and animals in vitro and in vivo. Such activities include, inter alia, thrombin-induced platelet aggregation, thrombin-induced calcium mobilization, thrombin-mediated coagulation, thrombin-induced cell motility and thrombin-induced cell adhesion. The compounds and methods of the invention are particularly relevant for use in humans and other mammals.

Another embodiment of this invention is to develop specific assays for high throughput screening of compounds that prevent binding of a labelled RPPGF (or a functional analog thereof) and/or thrombin cleavage and activation of the thrombin receptors PAR1 and PAR4. This embodiment includes a method for identifying a compound that inhibits or prevents thrombin- or thrombocytin-induced cleavage comprising the steps of i) contacting an extracellular fragment of PAR1 or PAR4 with an effective amount of thrombin or thrombocytin in the presence and absence of a test compound; and ii) measuring the amount of cleavage that occurs;

wherein a reduction in the amount of cleavage in the presence of said test compound is indicative of said test compound being an inhibitor of thrombin- or thrombocytin-induced cleavage.

This embodiment also includes a method for identifying a compound that inhibits or prevents binding of RPPGF (or a functional analog thereof) comprising the steps of
i) contacting an extracellular fragment of PAR1 or PAR4 with labeled RPPGF or a functional analog thereof in the presence and absence of a test compound; and
ii) measuring the amount of binding of said RPPGF or analog to said fragment;

wherein a reduction in the amount of binding in the presence of said test compound is indicative of said test compound being an inhibitor of RPPGF or analog binding.

By "functional analog" of RPPGF is meant a compound that is similar in structure and/or function to RPPGF and that binds to the extracellular fragment of PAR1 and/or PAR4. Such analogs include, for example, compounds of the invention and similar peptides that bind to the extracellular fragments.

The invention also includes a method of identifying a protease activated receptor 1 (PAR1) or protease activated receptor 4 (PAR4) binding agent comprising the steps of
i) contacting detectably labeled RPPGF (SEQ ID NO:4) with an extracellular fragment of PAR1 or PAR4 in the presence and absence of a test compound; and
ii) determining the amount of RPPGF that is bound to said fragment;

wherein a reduction in the amount of labeled RPPGF that is bound to the fragment in the presence of said test compound relative to the absence of said test compound is indicative of said test compound being a binding agent.

The invention also includes substitution and deletion mutants of the extracellular fragments of PAR1 and PAR4 that do not bind RPPGF or a functional analog. Deletion mutants wherein 1–5, preferably 3–4, residues are deleted are preferred. Two especially preferred embodiments of this aspect of the invention are deletion mutants of $rPAR1_{EC}$ lacking either the peptide sequence LDPR (SEQ ID NO:20) (Mutant IV) or PRSF (SEQ ID NO:15) (Mutant V). These mutants are characterized by substitution or deletion of the $P_2$ and/or $P_4$ positions of PAR1 and/or PAR4. Other mutants can be made by methods that are routine in the art. Such mutants are useful, inter alia, for elucidating structure-function relationships of the fragments and for functional screening of compounds that may affect thrombin activities.

The work leading to this invention has been disclosed in part in Hasan et al. *Amer. J Physiol Heart and Circ Physiol.*, In Press, July, 2003 (Published On-Line Feb. 21, 2003) This and all other publications cited herein are hereby incorporated by reference.

(Lys)-4(Arg-Pro-Pro-Gly-Phe)), TH146 (D-Arg-Oic-Pro-Gly-Phe), MAP4-TH146 (β-Ala-Lys-2(Lys)-4(D-Arg-Oic-Pro-Gly-Phe)), TH26 (D-Arg-Oic-Pro-Gly-Thi), TH34 (D-Arg-Oie-Pro-Gly-Idg), or TH37 (D-Arg-Oic-Hyp-Gly-Idg) was used to compete RPPGF-biotin (SEQ ID NO:13) binding to recombinant extracellular fragment of human PAR1.

Figure 8:
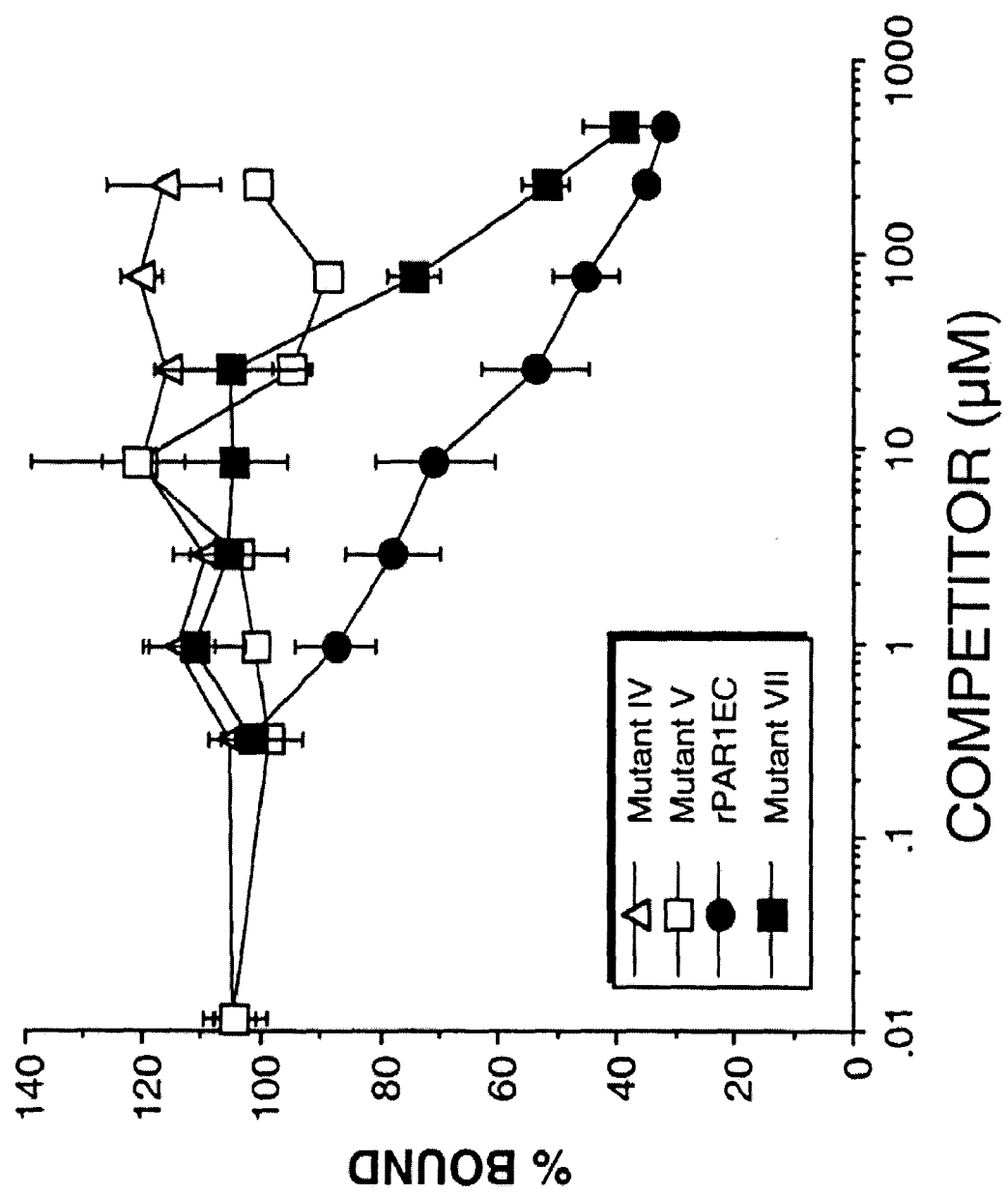

FIG. 8 illustrates what structural mutants of the extracellular fragment of human PAR1 compete RPPGF-biotin (SEQ ID NO:13) binding to recombinant extracellular fragment of human PAR1 ($rPAR1_{EC}$) bound to microtiter plates. Recombinant $PAR1_{EC}$ (1 µg/ml) was linked to microtiter plate cuvette wells in 0.1 M $Na_2CO_3$, pH 9.6 overnight at 4° C. After washing and blocking the wells with 1% bovine serum albumin, 10 µM RPPGF-biotin (SEQ ID NO:13) was added in the presence of increasing concentrations (0.3 to 500 µM) of wild-type $rPAR1_{EC}$ ($rPAR1_{EC}$), Mutant IV which is a recombinant $rPAR1_{EC}$ that has a deletion of the amino acids $Leu^{38}$-Asp-Pro-$Arg^{41}$ of the extracellular domain of human PAR1, Mutant V which is a recombinant $rPAR1_{EC}$ that has a deletion of the amino acids $Pro^{40}$-$Arg^{41}$-$Ser^{42}$-Phe of the extracellular domain of human PAR1, or Mutant VII which is a recombinant $rPAR1_{EC}$ that has a deletion of the amino acids $Trp^{52}$-Glu-Phe-$Tyr^{55}$ of the extracellular domain of human PAR1. Mutant IV and V have amino acids deletions adjacent to or at the thrombin cleavage site on human PAR1, respectively. Mutant VII has a deletion mutation at exosite I binding site on thrombin. These data indicate that when amino acids are deleted at or adjacent to the thrombin cleavage site, this recombinant does not block RPPGF-biotin (SEQ ID NO:13) binding to $rPAR1_{EC}$. These indicate that RPPGF (SEQ ID NO:4) binds to PAR1 at or near the thrombin cleavage site.

Figure 9:
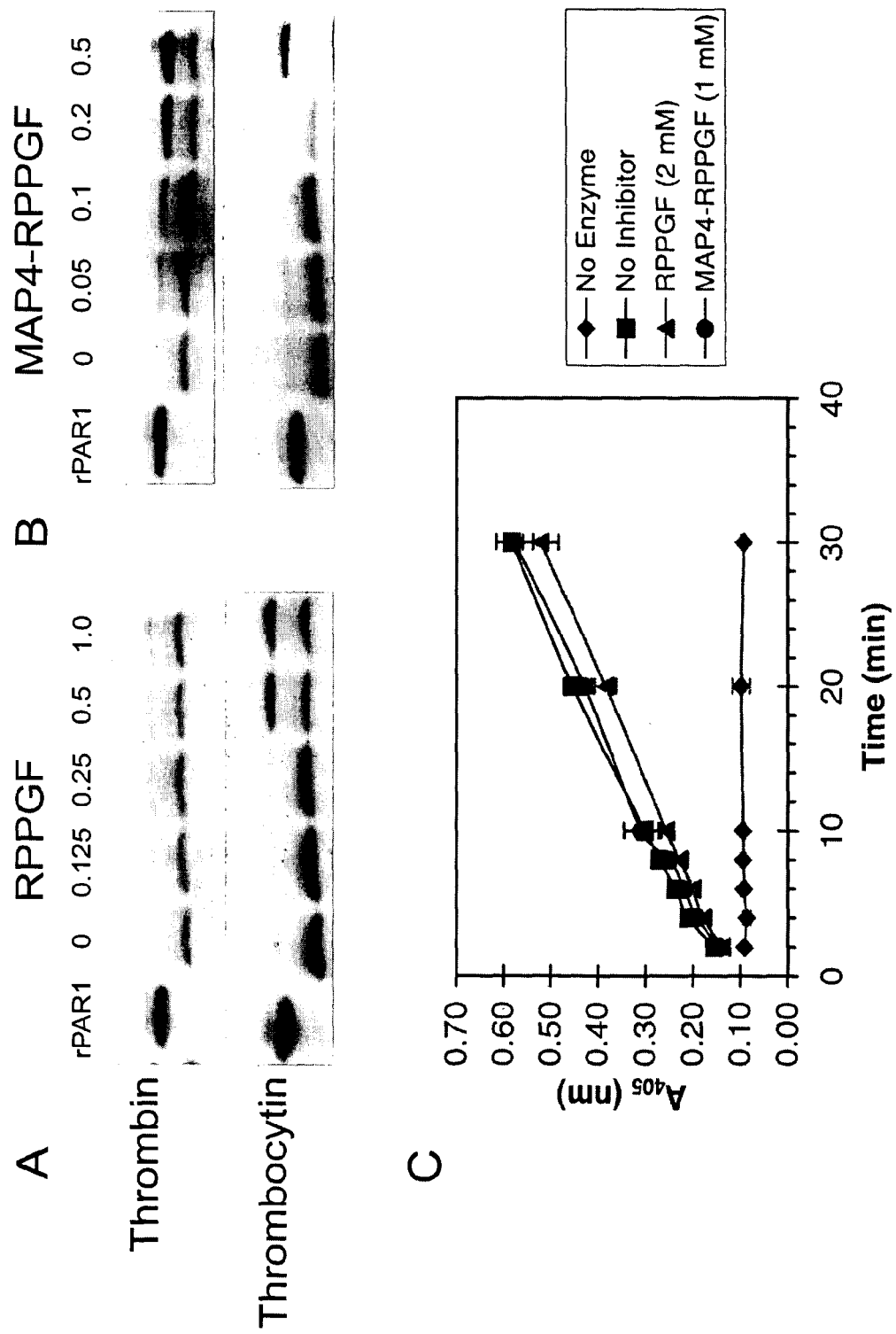

FIG. 9 examines the ability of RPPGF (SEQ ID NO:4) (Panel A) or MAP4-RPPGF (Panel B) to block thrombin or thrombocytin-induced proteolysis of recombinant extracellular fragment of human PAR1 ($rPAR1_{EC}$). In Panel A, 1 µg of $rPAR1_{EC}$ in 10 mM Tris-HCl, 200 mM NaCl, pH 8.0 was incubated at 37° C. for 15 min or 45 min with 1 nM α-thrombin or 0.5 µml (16.7 nM) thrombocytin, respectively, in the absence or presence of increasing concentrations of RPPGF (0.125 to 1.0 mM) (SEQ ID NO:4). Panel B: The ability of MAP4-RPPGF (β-Ala-Lys-2Lys-4(Arg-Pro-Pro-Gly-Phe) to inhibit the proteolytic cleavage of $rPAR1_{EC}$ by α-thrombin or thrombocytin. Recombinant $PAR1_{EC}$ was treated with α-thrombin or thrombocytin as in Panel A in the absence or presence of increasing concentrations of MAP4-RPPGF (0.05 to 0.5 mM). Panel C: The ability of thrombocytin (16.7 nM) to hydrolyze 1 mM H-D-Phe-Pip-Arg-paranitroanilide in the absence or presence of 2 mM RPPGF (SEQ ID NO:4) or 1 mM MAP4-RPPGF. The data indicate that RPPGF (SEQ ID NO:4) or MAP4-RPPGF inhibits the ability of these enzymes to hydrolyze their substrates and also prevents these enzymes from cleaving $rPAR1_{EC}$ at concentrations below that necessary to inhibit enzyme activity.

Figure 10:
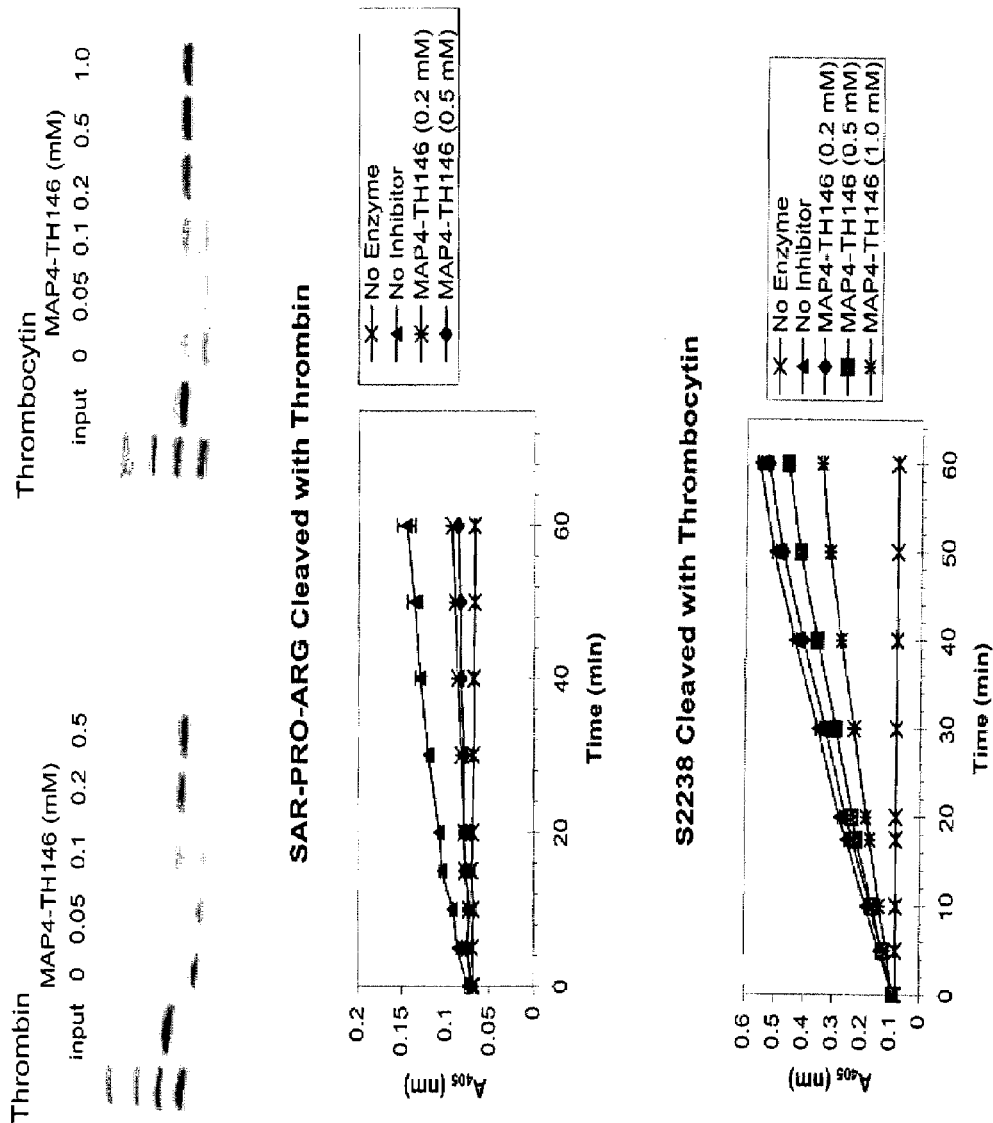

FIG. 10 examines the ability of MAP4-TH146 (β-Ala-Lys-2Lys-4(D-Arg-Oic-Pro-Gly-Phe)) to block thrombin or thrombocytin-induced proteolysis of recombinant extracellular fragment of human PAR1 ($rPAR1_{EC}$). In the upper Panels, 1 µg of $rPAR1_{EC}$ in 10 mM Tris-HCl, 200 mM NaCl, pH 8.0 was incubated at 37° C. for 15 min or 45 min with 1 nM α-thrombin or 0.5 µg/ml (16.7 nM) thrombocytin, respectively, in the absence or presence of increasing concentrations of MAP4-TH146 (0.05 to 1.0 mM)). In the middle Panel, the ability of α-thrombin (1 nM) to hydrolyze the chromogenic substrate Sar-Pro-Arg-pNA in the presence or absence of 0–0.5 mM MAP4-TH146 was determined. In the bottom Panel, the ability of thrombocytin (16.7 nM) to hydrolyze 1 mM H-D-Phe-Pip-Arg-paranitroanilide (S2238) in the presence or absence of 0–1.0 mM MAP4-TH146 was determined. The data indicate that MAP4-TH146 inhibits thrombin and thrombocytin cleavage of $rPAR1_{EC}$ (Upper Panel). In the middle Panel, MAP4-TH146 directly inhibits cleavage of $rPAR1_{EC}$ by directly blocking α-thrombin's proteolytic activity. Alternatively, in the bottom Panel, MAP4-TH146 inhibits thrombocytin proteolysis of $rPAR1_{EC}$ at concentrations below that necessary to block the proteolytic activity of the enzyme. These data indicate that MAP4-TH146 inhibits these enzymes' ability to hydrolyze their substrates and also prevents these enzymes from cleaving to $rPAR1_{EC}$ at concentrations below that necessary to inhibit directly the enzyme activity.

Figure 11:
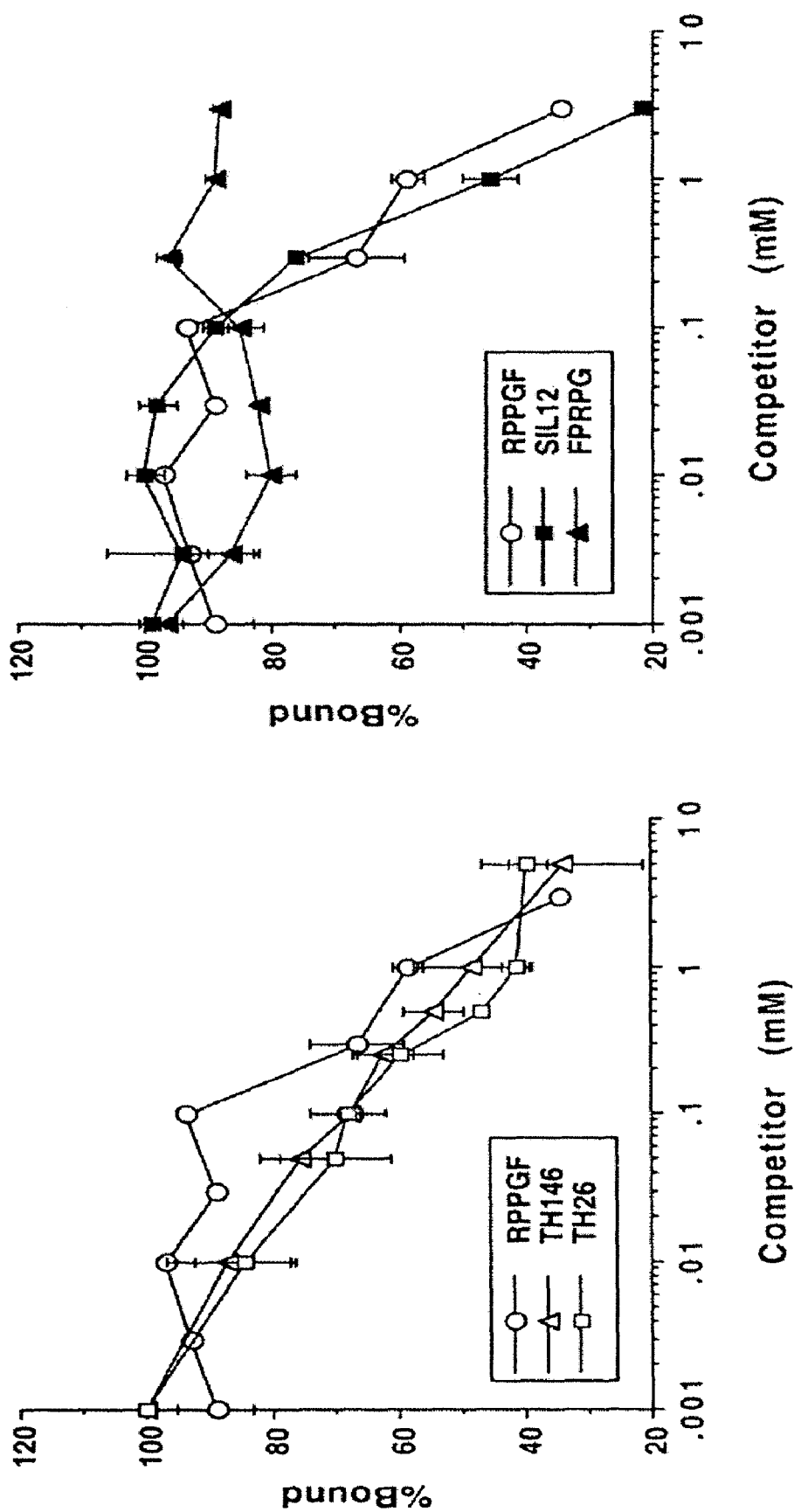

FIG. 11 illustrates the influence of various peptides on biotinylated-SIL12 (Ser-Ile-Leu-Pro-Ala-Pro-Arg-Gly-Tyr-Pro-Gly-Gln-biotin, SEQ ID NO:14) binding to RPPGC (SEQ ID NO:4) bound to plastic microtiter plates. In these experiments, 10 micromolar biotinylated-SIL12 (SEQ ID NO:14) was incubated in microtiter plate cuvette wells in the absence and presence of increasing concentrations (1 micromolar to 5 millimolar) of RPPGF (SEQ ID NO:4), TH146, TH26, SIL12 (SEQ ID NO:9), or FPRPG (SEQ ID NO:11). The per cent inhibition of biotinylated SIL12 (SEQ ID NO:14) binding is shown.

Figure 12:
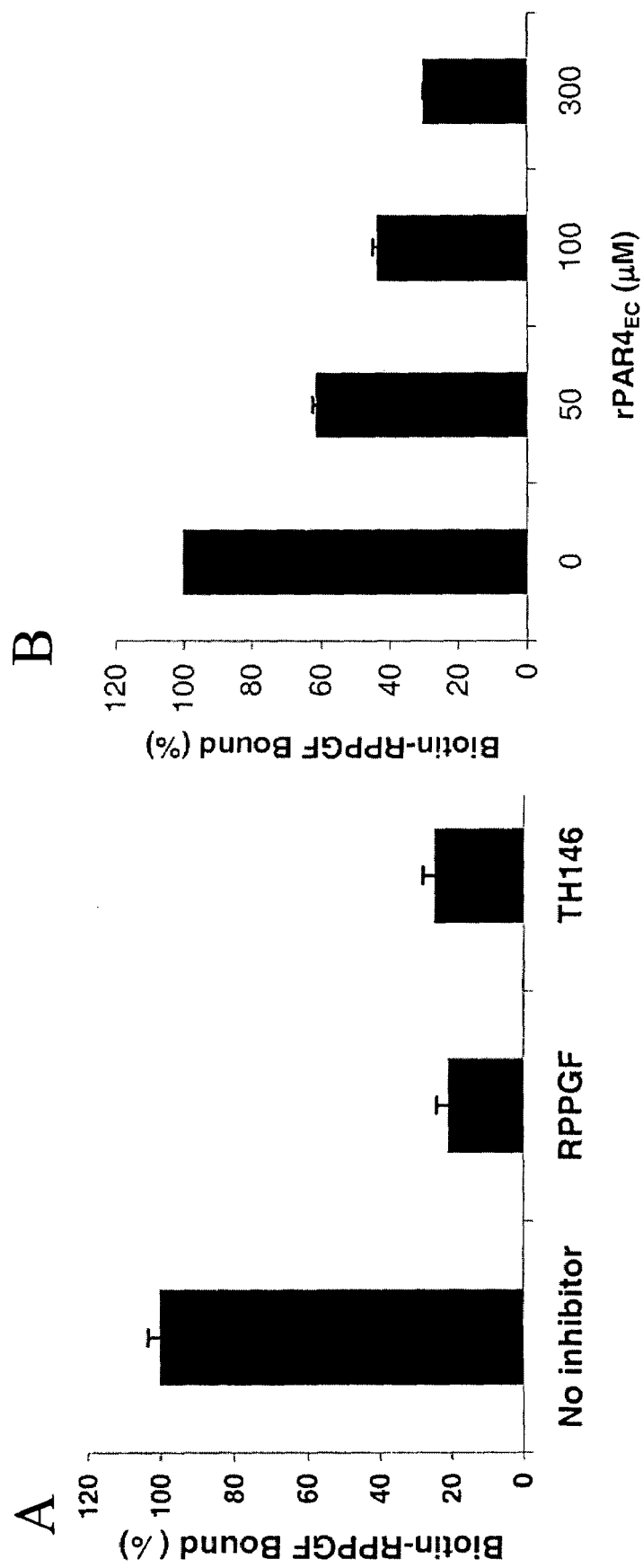

FIG. 12 examines the ability of RPPGF (SEQ ID NO:4) or TH146 to inhibit RPPGF-biotin (SEQ ID NO:13) from directly binding to recombinant, extracellular fragment of human protease activated receptor 4 ($rPAR4_{EC}$) bound to microtiter plate cuvette wells. In Panel A, 50 micromolar biotinylated RPPGF (SEQ ID NO:4) was incubated with microtiter plate cuvette wells that have recombinant, extracellular fragment of human protease activated receptor 4 bound at 1 µg/ml in the absence or presence of 5 mM RPPGF (SEQ ID NO:4) or TH146. The values shown are the percent biotin-RPPGF ((SEQ ID NO:4) bound in the absence (No inhibitor) or presence of RPPGF (SEQ ID NO:4) or TH146. In Panel B, 15 micromolar biotinylated RPPGF (SEQ ID NO:4) was incubated with microtiter plate cuvette wells that have recombinant, extracellular fragment of human protease activated receptor 4 bound at 1 µg/ml in the absence or presence of 50–300 µM $rPAR4_{EC}$. The per cent biotin-RPPGF (SEQ ID NO:4) bound is shown.

Figure 13:
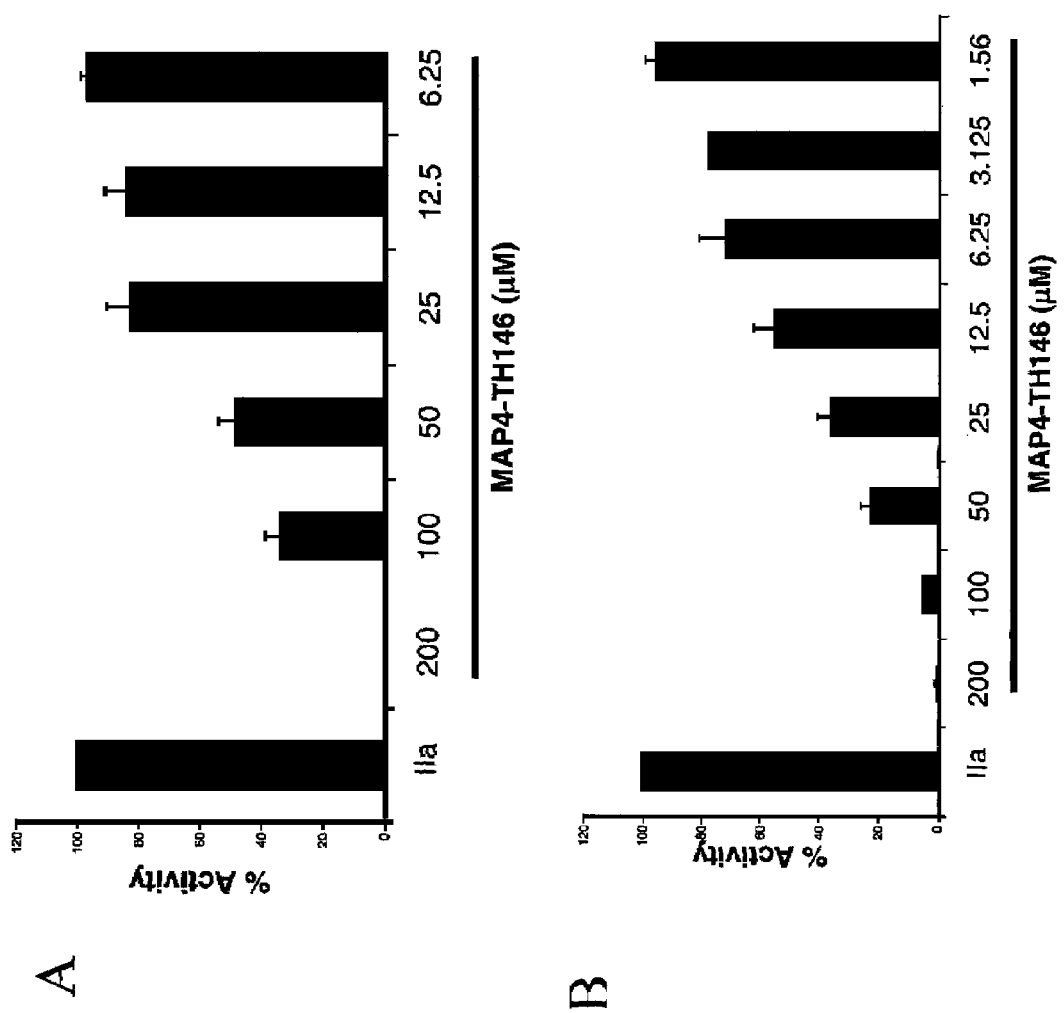

FIG. 13 examines the influence of MAP4-TH146 on thrombin-induced calcium mobilization in two prostate cancer cell lines that functionally express PAR 1. In Panel A, the influence of MAP4-TH146 on 2 nM α-thrombin-induced intracellular calcium mobilization in VCaP cells. Calcium flux is abolished by 200 MAP4-TH146. At 6.25 µM MAP4-TH146, there is full recovery of thrombin-induced calcium flux. In Panel B, the influence of MAP4-TH146 on 2 nM α-thrombin-induced intracellular calcium mobilization in PC3 cells. Calcium flux is abolished by 200 μM MAP4-TH146. At 1.56 μM MAP4-TH146, calcium flux recovers.

Figure 14:
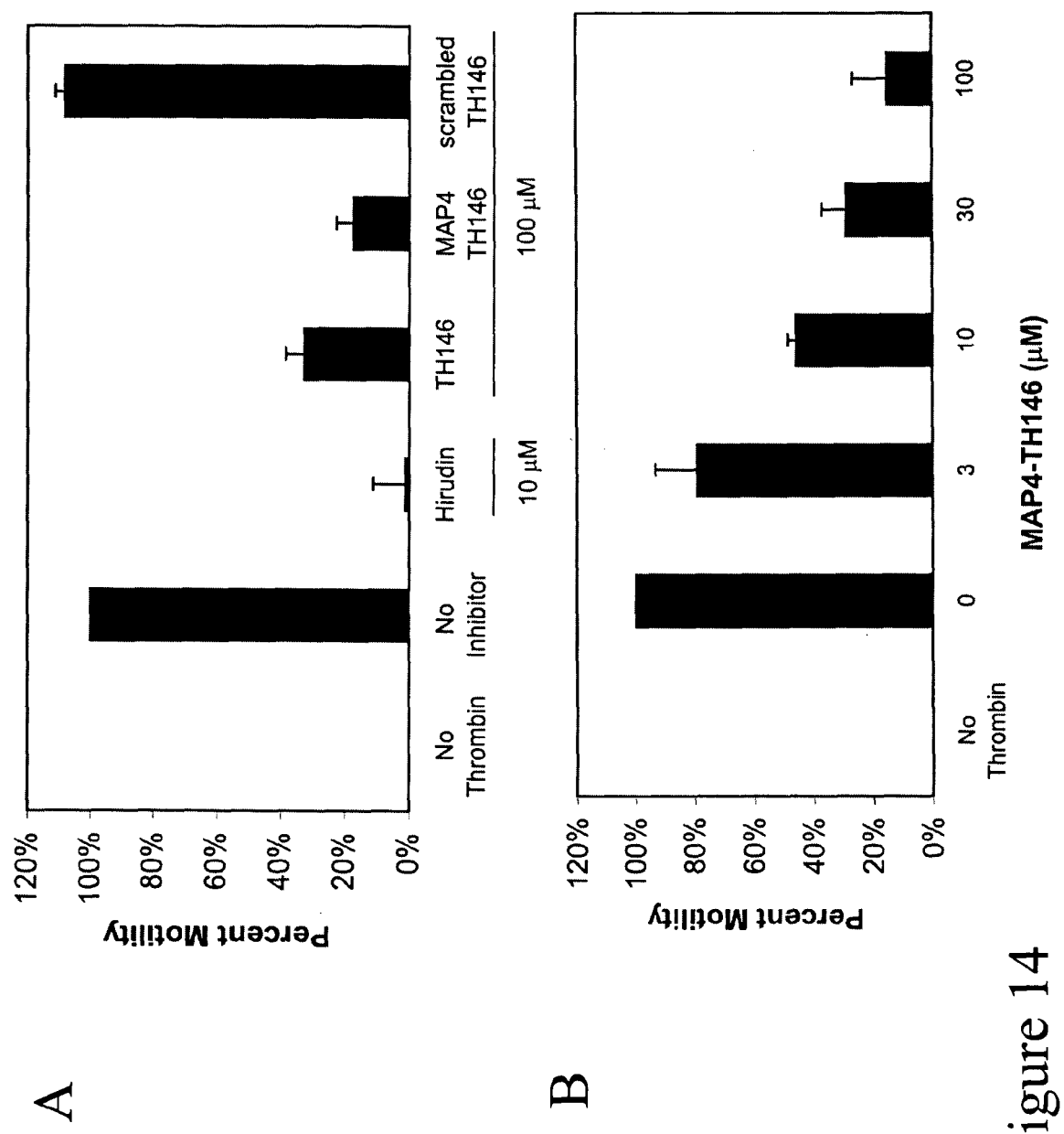

FIG. 14 examines the influence of MAP4-TH146 on 2 nM α-thrombin-induced PC-3 cell motility in a Boydan chamber. In Panel A, both TH146 and MAP4-TH146 both at 100 μM block thrombin-induced PC-3 cell motility along with 10 μM hirudin. However, a scrambled peptide of TH146 does not block PC-3 cell motility. In Panel B, TH146 blocks α-thrombin-induced PC-3 cell motility in a concentration-dependent manner from 3–100 μM concentration. These data indicate that α-thrombin stimulates PC-3 cell motility and TH146 and MAP4-TH146 block it.

Table I is a tabulation of the library of peptides prepared and the influence of each peptide on γ-thrombin-induced platelet aggregation in platelet-rich plasma. The numbers in the column represent the minimal concentration (mM) of the peptide that blocked γ-thrombin-induced platelet aggregation of platelets in platelet-rich plasma.

TABLE I

Effect of Peptide library on Thrombin-Induced Platelet Aggregation

| Peptide | Concentration of Peptide [mM] That Gives 100% Inhibition | SEM |
|---|---|---|
| rOicPGF | 0.142 | 0.02 |
| MAP4-rOicPGF | 0.019 | 0.006 |
| rOicPGIdg | 0.129 | 0.02 |
| rOicHypGThi | 0.157 | 0.02 |
| rOicHypGIdg | 0.157 | 0.02 |
| rOicPGThi | 0.228 | 0.02 |
| rOicOicGIdg | 0.257 | 0.04 |
| rOicOicGThi | 0.271 | 0.04 |
| rIdgTicGF | 0.1 | |
| RPOicGF (SEQ ID NO:29) | 0.113 | |
| rOicOicGF | 0.140 | |
| rPTicGThi | 0.15 | |
| rOicHypGF | 0.153 | |
| rOicTicGF | 0.2 | |
| tTicIdgGF | 0.2 | |
| rPPGThi | 0.2 | |
| rTicPGF | 0.2 | |
| rTicF5FGF | 0.2 | |
| rF5FticGF | 0.2 | |
| rPPGIdg | 0.2 | |
| rROicOicGF | 0.25 | |
| rRHypOicGF | 0.5 | |
| rROicHypGF | 0.5 | |
| rOicPGF | 0.5 | |
| RoicOicGF | 0.5 | |
| rPPGF | 0.5 | |
| rRPHypGF | 0.5 | |
| rPHypGF | 0.6 | |
| RHypOicGF | 0.6 | |
| ROicHypGF | 0.6 | |
| ROicPGF (SEQ ID NO:28) | 0.6 | |
| rRHypPGF | 1.0 | |
| rRHypHypGF | 1.0 | |
| rHypHypGF | 1.0 | |
| rPOicGF | 1.0 | |
| RPHypGF (SEQ ID NO:30) | 1.0 | |
| rIdgIdgGF | No Effect | |
| rF5FidgGF | No Effect | |
| RTicPGThi | No Effect | |
| RPOicGThi | No Effect | |
| rPF5FGF | No Effect | |
| rOicF5FGF | No Effect | |
| rRPPGF | No Effect | |
| rHypPGF | No Effect | |
| rHypOicGF | No Effect | |
| RHypPGF (SEQ ID NO:31) | No Effect | |
| RhypHypGF | No Effect | |
| rIdgPGF | No Effect | |
| rPIdgGF | No Effect | |
| rOicIdgGF | No Effect | |
| rIdgOicGF | No Effect | |
| rF5FPGF | No Effect | |
| rF5FoicGF | No Effect | |
| rIdgF5FGf | No Effect | |
| rPTicGF | No Effect | |
| rTicTicGF | No Effect | |
| rTicOicGF | No Effect | |
| rIdgPGThi | No Effect | |
| rPIdgGThi | No Effect | |
| rROicPGOic | No Effect | |
| rROicPGTic | No Effect | |
| rROicPG5F5 | No Effect | |
| rROicPGHyp | No Effect | |
| rROicHypGOic | No Effect | |
| rROicHypGThi | No Effect | |
| rROicHypG5F5 | No Effect | |
| rROicHypGHyp | No Effect | |
| rROicOicGOic | No Effect | |
| rROicOicGTic | No Effect | |
| rROicOicG5F5 | No Effect | |
| rROicOicGHyp | No Effect | |

Table II is a tabulation of the library of peptides and the influence of each peptide on α-thrombin-induced calcium mobilization in fibroblasts. The numbers in the column under "$Ca^{2+}$% Inhibition" represent the degree of inhibition of thrombin-induced calcium mobilization by 0.1 mM peptide.

TABLE II

Inhibition of Thrombin-Induced Calcium Mobilization by Peptides of the Peptide Library

| Peptide | $Ca^{2+}$ % Inhibition At 0.1 mM Peptide |
|---|---|
| rOicPGF | 54 |
| MAP4-rOicPGF | |
| rOicPGIdg | 36.2 |
| rOicHypGThi | 38 |
| rOicHypGIdg | 36.7 |
| rOicPGThi | 14.5 |
| rOicOicGIdg | 28.1 |
| rOicOicGThi | 18.2 |
| rIdgTicGF | 58.44 |
| RPOicGF (SEQ ID NO:29) | No Effect |
| rOicOicGF | 29 |
| rPTicGThi | No Effect |
| rOicHypGF | 34 |
| rOicTicGF | No Effect |
| tTicIdgGF | No Effect |
| rRPPGThi | No Effect |
| rTicPGF | No Effect |
| rTic5F5GF | No Effect |
| rF5FticGF | No Effect |
| rPPGIdg | No Effect |
| rROicOicGF | No Effect |
| rRPOicGF | No Effect |
| rRHypOicGF | No Effect |
| rROicHypGF | No Effect |
| ROicOicGF | No Effect |
| rPPGF | No Effect |
| rRPHypGF | No Effect |
| RPHypGF (SEQ ID NO:30) | No Effect |
| RHypOicGF | No Effect |
| ROicHypGF | No Effect |
| ROicPGF (SEQ ID NO:28) | No Effect |
| rRHypPGF | No Effect |

TABLE II-continued

Inhibition of Thrombin-Induced Calcium Mobilization by Peptides of the Peptide Library

| Peptide | Ca$^{2+}$ % Inhibition At 0.1 mM Peptide |
|---|---|
| rRHypHypGF | No Effect |
| rHypHypGF | No Effect |
| rPOicGF | No Effect |
| RPHypGF (SEQ ID NO:30) | No Effect |
| rIdgIdgGF | 73 |
| rF5FIdgGF | 32 |
| RTicPGThi | 45 |
| rPOicGThi | 15 |
| rPF5FGF | 11 |
| rOicF5FGF | 2.6 |
| rRPPGF | No Effect |
| rHypPGF | No Effect |
| rHypOicGF | No Effect |
| RHypPGF (SEQ ID NO:31) | No Effect |
| RHypHypGF | No Effect |
| rIdgPGF | No Effect |
| rPIdgGF | No Effect |
| rOicIdgGF | No Effect |
| rIdgOicGF | No Effect |
| rF5FPGF | No Effect |
| rF5FOicGF | No Effect |
| rIdgF5FGf | No Effect |
| rPTicGF | No Effect |
| rTicTicGF | No Effect |
| rTicOicGF | No Effect |
| rIdgPGThi | No Effect |
| rPIdgGThi | No Effect |
| rROicPGOic | No Effect |
| rROicPGTic | No Effect |
| rROicPG5F5 | No Effect |
| rROicPGHyp | No Effect |
| rROicHypGOic | No Effect |
| rROicHypGThi | No Effect |
| rROicHypG5F5 | No Effect |
| rROicHypGHyp | No Effect |
| rROicOicGOic | No Effect |
| rROicOicGTic | No Effect |
| rROicOicGF5F | No Effect |
| rROicOicGHyp | No Effect |

Table III is a tabulation of the library of peptides and the influence of each peptide at the concentration that inhibits platelet aggregation on the coagulation assays of the APTT (activated partial thromboplastin time), PT (prothrombin time) and TCT (thrombin clotting time).

TABLE III

Inhibition of Coagulant Activity by Peptides of the Peptide Library

| Peptide | APTT | PT | TCT |
|---|---|---|---|
|  | (Fold Prolongation over RPPGF) | | |
| rOicPGF | 1.3 | 1.1 | 1.5 |
| MAP4-rOicPGF | | | |
| rOicPGIdg | 1.1 | 1.1 | 1.5 |
| rOicHypGThi | 1.1 | 1.1 | 1.3 |
| rOicHypGIdg | 1.1 | 1.1 | 1.7 |
| rOicPGThi | 1.1 | 1.0 | 1.4 |
| rOicOicGIdg | 1.1 | 1.1 | 1.1 |
| rOicOicGThi | 1.2 | 1.1 | 1.1 |
| rIdgTicGF | 1.0 | 1.1 | 1.2 |
| RPOicGF (SEQ ID NO:29) | 1.1 | 1.0 | 1.5 |
| rOicOicGF | 1.4 | 1.2 | 1.5 |
| rPTicGThi | 1.0 | 1.0 | 1.1 |
| rOicHypGF | 1.4 | 1.2 | 1.7 |
| rOicTicGF | 1.3 | 1.1 | 1.6 |
| rTicIdgGF | 1.0 | 1.2 | 1.0 |
| rPPGThi | 1.2 | 1.1 | 1.2 |

TABLE III-continued

Inhibition of Coagulant Activity by Peptides of the Peptide Library

| Peptide | APTT | PT | TCT |
|---|---|---|---|
|  | (Fold Prolongation over RPPGF) | | |
| rTicPGF | 1.1 | 1.1 | 1.2 |
| rTicF5FGF | 1.0 | 1.1 | 1.0 |
| rF5FTicGF | 1.0 | 1.0 | 1.0 |
| rPPGIdg | 1.1 | 1.0 | 1.0 |
| rROicOicGF | 1.1 | 1.0 | 1.0 |
| rRPOicGF | 1.1 | 1.0 | 1.3 |
| rRHypOicGF | 1.1 | 1.0 | 1.0 |
| rROicHypGF | 1.0 | 1.0 | 1.1 |
| ROicOicGF | 1.2 | 1.1 | 1.3 |
| rPPGF | 1.0 | 1.0 | 1.0 |
| rRPHypGF | 1.1 | 1.0 | 1.0 |
| rPHypGF | 1.0 | 1.0 | 1.1 |
| RHypOicGF | 1.1 | 1.0 | 1.1 |
| ROicHypGF | 1.2 | 1.2 | 1.1 |
| ROicPGF (SEQ ID NO:28) | 1.2 | 1.1 | 1.7 |
| rRHypPGF | 1.3 | 1.0 | 1.1 |
| rRHypHypGF | 1.0 | 1.0 | 1.1 |
| rHypHypGF | 1.1 | 1.0 | 1.2 |
| rPOicGF | 1.1 | 1.1 | 1.2 |
| RPHypGF | 1.5 | 1.2 | 2.1 |
| rIdgIdgGF | 1.0 | 1.0 | 1.0 |
| rF5FIdgGF | 1.0 | 1.0 | 1.0 |
| RTicPGThi | 1.0 | 1.0 | 1.0 |
| rPOicGThi | 1.0 | 1.0 | 1.0 |
| rPF5FGF | 1.0 | 1.0 | 1.0 |
| rOicF5FGF | 1.0 | 1.0 | 1.0 |
| rRPPGF | 1.0 | 1.0 | 1.0 |
| rHypPGF | 1.0 | 1.0 | 1.0 |
| rHypOicGF | 1.0 | 1.0 | 1.0 |
| RHypPGF (SEQ ID NO:31) | 1.0 | 1.0 | 1.0 |
| RHypHypGF | 1.0 | 1.0 | 1.0 |
| rIdgPGF | 1.0 | 1.0 | 1.0 |
| rPIdgGF | 1.0 | 1.0 | 1.0 |
| rOicIdgGF | 1.0 | 1.0 | 1.0 |
| rIdgOicGF | 1.0 | 1.0 | 1.0 |
| rF5FPGF | 1.0 | 1.0 | 1.0 |
| rF5FOicGF | 1.0 | 1.0 | 1.0 |
| rIdgF5FGf | 1.0 | 1.0 | 1.0 |
| rPTicGF | 1.0 | 1.0 | 1.0 |
| rTicTicGF | 1.0 | 1.0 | 1.0 |
| rTicOicGF | 1.0 | 1.0 | 1.0 |
| rIdgPGThi | 1.0 | 1.0 | 1.0 |
| rPIdgGThi | 1.0 | 1.0 | 1.0 |
| rROicPGOic | 1.0 | 1.0 | 1.2 |
| rROicPGTic | 1.1 | 1.0 | 1.1 |
| rROicPGF5F | 1.1 | 1.1 | 1.0 |
| rROicPGHyp | 1.1 | 1.0 | 1.1 |
| rROicHypGOic | 1.0 | 1.0 | 1.2 |
| rROicHypGThi | 1.0 | 1.0 | 1.0 |
| rROicHypG5F5 | 1.2 | 1.0 | 1.2 |
| rROicHypGHyp | 1.1 | 1.0 | 1.1 |
| rROicOicGOic | 1.1 | 1.0 | 1.0 |
| rROicOicGTic | 1.0 | 1.0 | 1.0 |
| rROicOicGF5F | 1.0 | 1.0 | 1.2 |
| rROicOicGHyp | 1.0 | 1.0 | 1.0 |

Table IV is a tabulation of 21 naturally occurring amino acids.

TABLE IV

Naturally Occurring Amino Acids

| Amino Acid | Three-letter abbreviation | One-letter symbol |
|---|---|---|
| Alanine | Ala | A |
| Arginine | Arg | R |
| Asparagine | Asn | N |
| Aspartic Acid | Asp | D |
| Cysteine | Cys | C |
| Glutamine | Gln | Q |

TABLE IV-continued

Naturally Occurring Amino Acids

| Amino Acid | Three-letter abbreviation | One-letter symbol |
| --- | --- | --- |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

Table V is a tabulation of 9 synthetic amino acids used to make the compounds shown in Tables I–III.

TABLE V

Synthetic Amino Acids Used to Prepare Peptides

| Amino Acid | 3 Letter Abbreviation | letter symbol |
| --- | --- | --- |
| D-arginine | D-Arg | r |
| D-phenylalanine | D-Phe | f |
| Hydroxyproline | Hyp | — |
| α-(2-indanyl)glycine | Idg | — |
| (2S, 3aS, 7aS)-octahydroindole-2-carboxlic acid | Oic | — |
| 1,2,3,4-tetrahydroisoquinoline-3-carboxylic acid | Tic | — |
| β-(2-thienyl)-L-alanine | Thi | — |
| Pentafluorophenylalanine | F5F | — |

DETAILED DESCRIPTION OF THE INVENTION

Definitions

"Natural amino acid" means any of the twenty primary, naturally occurring amino acids which typically form peptides, polypeptides, and proteins.

"Synthetic amino acid" means any other amino acid, regardless of whether it is prepared synthetically or derived from a natural source. As used herein, "synthetic amino acid" also encompasses chemically modified amino acids, including but not limited to salts, derivatives (such as amides), and substitutions.

The invention relates to the peptide analogs of Formulae I, II, and III above.

Peptides of the invention are produced by conventional solid phase peptide synthesis techniques using automated synthesis.

In accordance with the present invention naturally occurring or synthetic amino acids having the general formula $^{31}CO_2(RCHCH(NH_3)^+$ are produced by addition of the group to either the carboxyl or amino terminus of a peptide comprising the core sequence in order to form chain expansion analogs. The peptides of Formula I, Formula II, or Formula III comprise at most six (6) amino acids in sequence. Preferably, the peptide compound and the segment comprise five amino acids in sequence.

The general approach for the preparation of these peptides was to substitute non-natural amino acids for natural amino acids to create compounds that would not be metabolized as peptides with naturally occurring amino acids.

Peptide analogs of RPPGF (Arg-Pro-Pro-Gly-Phe, SEQ ID NO:4) were prepared by traditional solid-phase peptide synthesis (Merrifield R B. *J. Amer. Chem. Soc.* 85, 2149–2154 (1963)) in conjunction with the "tea-bag" methodology (Houghten R A. *Proc. Natl. Acad. Sci.* 82, 5131–5135 (1985)) using Boc/benzyl based chemistry. The peptides were assembled on Methylbenzhydrylamine resin (MBHA resin) using traditional Boc/Benzyl based chemistry. The protected amino acids were Boc-Arg (Tos), Boc-D-Arg (Tos), Boc-Gly, Boc-Phe, Boc-Pro, Boc-F5F, Boc-Hyp, Boc-Idg, Boc-Oic, Boc-Tic, and Boc-Thi with Boc being tert-butyloxycarbonyl, F5F being Pentafluorophenylanine, Hyp being L-4-Hydroxyproline, Idg being α-(2-indanyl)glycine, Oic being Octhydroindole-2-carboxylic acid, Tic being Tetrahydroisoquinoline-3-carboxylic acid, Thi being β-(20Thienyl)-alanine, and Tos being Tosyl. In order to begin the synthesis, bags made of a polypropylene mesh material are filled with resin. The bags are then placed in a Nalgene bottle with dichloromethane (DCM) and shaken 5 min to allow the swelling of the resin. The DCM solution is then discarded and the actual synthesis is performed. The resin packets were washed 3 times, 2 minutes each time, with 5% diisopropylethylamine (DIEA) in DCM (neutralization step) then with DCM (2×1 min) to remove excess base. After neutralization, the packets are sorted and placed in Nalgene bottles containing the amino acid of interest in DCM. An equal amount of activator [diisopropylcarbodiimide (DIC)] in DCM is added and the coupling reaction is started. After shaking for 1 h, the packets are washed twice with DMF followed by a final two washes with DCM. The N-α-t-Boc is removed by acidolysis using 55% trifluoroacetonitril (TFA) in DCM for 30 min, leaving a TFA salt of the α-amino group. The bags are then washed successively with DCM (1×1 min), isopropanol (2×1 min) and DCM (1×1 min) to remove any residual TFA. This procedure is repeated for the addition of each amino acid at the coupling step. After completion of the synthesis and final tert-butyloxycarbonyl (Boc) removal, the peptides are side chain deprotected and cleaved from the resin at 0° C. with liquid hydrogen fluoride (HF) in the presence of anisole as a carbocation scavenger. The procedure is performed in a 10-vessel HF apparatus (Houghten et al. *Int. J. Peptide Res.* 27, 673–678 (1985)). The reaction is allowed to proceed for 60 min. Liquid HF is then removed using a strong flow of $N_2$ for 90 min followed by the use of aspirator vacuum for 60 min while maintaining the temperature at 0° C. The reaction vessels were disconnected from the apparatus and the residual anisole was removed from the resin with two ethylether washes. The peptides are then extracted with 10% acetic hydroxide washes and the extraction solutions are pooled and lyophilized. The crude peptides are weighed and stored under nitrogen and subsequently analyzed by analytical RP-HPLC and by mass spectral analysis.

Preparation of MAP4-rOicPGF (β-Ala-Lys-2Lys-4(D-Arg-Oic-Pro-Gly-Phe)) "MAP" is an acronym for "multiple antigenic peptide". A four-branch MAP of rOicPGF (D-Arg-Oic-Pro-Gly-Phe), hereinafter called "MAP4-rOicPGF" was prepared. The structure of MAP4-rOicPGF is as follows:

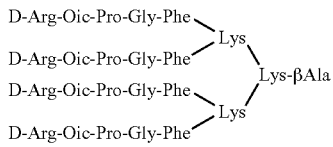

To prepare MAP4-rOicPGF, a resin core, having β-alanine attached through its carboxyl group, is joined to a free carboxyl of lysine through the free amine of β-alanine (βAla) to form a lysine-β-alanine complex. Two additional lysine residues were then attached by their free carboxyl groups to the two free amines of the first lysine. Four molecules of rOicPGF (D-Arg-Oic-Pro-Gly-Phe) are then attached through their phenylalanine residues to the free amino groups of the two lysines residues, following activation of the carboxy groups with 2(1-H-benzotriazole-1-YL)-1,1,3,3-tetramethyl-uroniumhexofluorophosphate (HBTU) and 1-hydroxybenzotriazole (HOBt). A fluorenyl-methyloxycarbonyl moiety is then attached at the aminoterminal end as a blocking group. The MAP4-rOicPGF was purified by reverse phase HPLC and then characterized by mass spectroscopy.

This invention is directed to a method for preventing thrombosis using peptide analogs that act as selective antithrombins. These peptide analogs are selective antithrombins because they are able to directly interact with human α-thrombin or γ-thrombin at their active site and are able to inhibit human α-thrombin or γ-thrombin from cleaving PAR1 or PAR4 at its thrombin cleavage site to prevent thrombin induced stimulus-response coupling and activation of platelets and other normal or cancerous cells. These compounds bind to PAR1 at the sequence LDPR[41] (Leu-Asp-Pro-Arg, SEQ ID NO:7) or PRSF[43] (Pro-Arg-Ser-Phe, SEQ ID NO:15) and prevent thrombin from cleaving PAR1 between its Arg[41] and Ser[42]. These compounds also bind to human PAR4 to do the same thing. The relative concentrations of thrombin to platelets used to induce platelet activation or aggregation ranged from about 0.25 to about 3 nM of α-thrombin or about 15 to 70 nM of γ-thrombin. Compounds of Formula I, Formula II, and Formula III achieve selectivity in inhibiting thrombin activation by being directed to both a substrate of thrombin (PAR1 or PAR4) and the enzyme itself. Most known thrombin inhibitors, hirudin, hirugen, argatroban, bivalirudin interfere with α-thrombin's action only by interacting with thrombin itself at its active site and/or exosite I. Use of these known proteolytic inhibitors to block α-or γ-thrombin activation of platelets and other cells expressing PAR1 or PAR4 may result in excessive anticoagulation, hemorrhage, and interference with other important biologic activities such as mitogenesis and cell proliferation. The peptide analogs utilized in the present method allow for inhibition of thrombin-induced platelet or other cell stimulus-response coupling and activation mediated by two substrates of thrombin, PAR1 and PAR4, without interfering with some of the other α-thrombin activities such as activation of factors V and XIII.

We have found that the peptides described herein bind to both PAR1 and PAR4 and inhibit thrombin cleavage of the thrombin receptor (PAR1) which is expressed on human platelets, fibroblasts and other normal or cancerous human cells. The peptides described herein also inhibit thrombin activation of mouse platelets—platelets that only express PAR4. Thus, we have found that the peptides described here have the ability to inhibit thrombin-induced platelet activation by blocking thrombin itself and thrombin cleavage of PAR1 and PAR4 and subsequent activation of platelets by exposure of the new amino terminus of the cleaved receptor. Administration of a peptide analog described herein comprises a method for inhibiting thrombin-induced activation of platelets, endothelial cells, brain cells, fibroblasts, smooth muscle cells, or other normal or cancerous cells that contain the PAR1 and/or PAR4 receptor for thrombin. The activity of this peptide inhibitor blocks platelet thrombus formation, calcium flux in many cells, and other activities mediated by the thrombin receptor.

The peptide analogs described here do not inhibit platelet activation by the same mechanism as intact kininogens or isolated domain 3. One mM peptide analogs do not block $^{125}$I-α-thrombin binding to platelets, as do molar excess purified HK, LK, or isolated domain 3. We have found that these peptide analogs:

1) block α-thrombin-induced calcium mobilization in fibroblasts;
2) block γ-thrombin-induced platelet aggregation in human and mouse platelets; and
3) prevents thrombocytin cleavage of rPAR1$_{EC}$ (a recombinant portion of the extracellular domain of human protease activated receptor 1) at concentrations below those necessary to inhibit the active site of the enzyme.

According to one embodiment of the invention, these peptide analogs represent an amino acid substitution in any one or more of the five positions of the parent peptide so that the resulting compound exhibits the desired activity.

Ala[26]-Arg-Arg-Pro-Glu-Ser-Lys-Ala-Thr-Asn-Ala-Thr-Leu-Asp-Pro-Arg-Ser-Phe-Leu- (SEQ ID NO:16)

Leu-Arg-Asn-Pro-Asn-Asp-Lys-Tyr-Glu-Pro-Phe-Trp-Glu-Asp-Glu-Glu-Lys-Asn-Glu-

Ser-Gly-Leu-Thr-Glu-Tyr-Arg-Leu-Val-Ser-Ile-Asn-Lys-Ser-Ser-Pro-Leu-Gln-Lys-Gln-

Leu-Pro-Ala-Phe-Ile-Ser-Glu-Asp-Ala-Ser-Gly-Tyr-Leu-Thr-Ser-Ser[99]

The following sequence of recombinant extracellular domain of PAR1(rPAR1 $_{EC}$) from alanine[26] to serine[99] was used to screen the present peptide antagonists:

This sequence was derived from Vu et al. *Cell* 64, 1057 (1991).

The following sequence of recombinant extracellular domain of PAR4 (rPAR4$_{EC}$) from glycine[18] to arginine[78] was also used to screen the present peptide antagonists:

Gly[18]-Gly-Thr-Gln-Thr-Pro-Ser-Val-Tyr-Asp-Glu-Ser-Gly-Ser-Thr-Gly-Gly-Gly-Asp- (SEQ ID NO:24)

Asp-Ser-Thr-Pro-Ser-Ile-Leu-Pro-Ala-Pro-Arg-Gly-Trp-Pro-Gly-Gln-Val-Cys-Ala-Asn-

Asp-Ser-Asp-Thr-Leu-Glu-Leu-Pro-Asp-Ser-Ser-Arg-Ala-Leu-Leu-Leu-Gly-Trp-Val-

Pro-Thr-Arg[78]

This sequence is from Xu et al. *Proc. Natl. Acad. Sci.* 95, 6642 (1998).

I. Preparation of Peptide Analogs that Interfere with Thrombin-Induced Platelet Aggregation

A. Assays to Screen Peptide Libraries

Five assays were developed to screen peptides produced by the methods described above

1. Platelet Aggregation

Fresh whole blood was collected and mixed with 0.013 M sodium citrate and platelet-rich plasma was prepared according to the method of Meloni et al., *J. Biol. Chem.* 266, 6786 (1991). Platelet-rich plasma with a normalized platelet count between 2–2.5×10⁸ platelets/ml was added to a cuvette of an aggregometer (Chronlog Corp., Havertown, Pa.), standardized using the protocol of Meloni et al., supra. Peptides to be examined were added to the cuvette and the mixture stabilized for a few moments. Once the baseline was stabilized, γ-thrombin (10–70 nM) (Haematologic Technologies, Essex Junction, Vt.) was added to determine the minimal concentration of the agonist necessary to achieve full platelet aggregation. All investigations with peptides were performed using threshold concentrations of γ-thrombin. Aggregation was allowed to proceed for 5 minutes before stopping. When ADP-induced platelet aggregation studies were performed, 1–5 μM ADP (Sigma) was added to the cuvette containing platelet-rich plasma.

Figure 1:
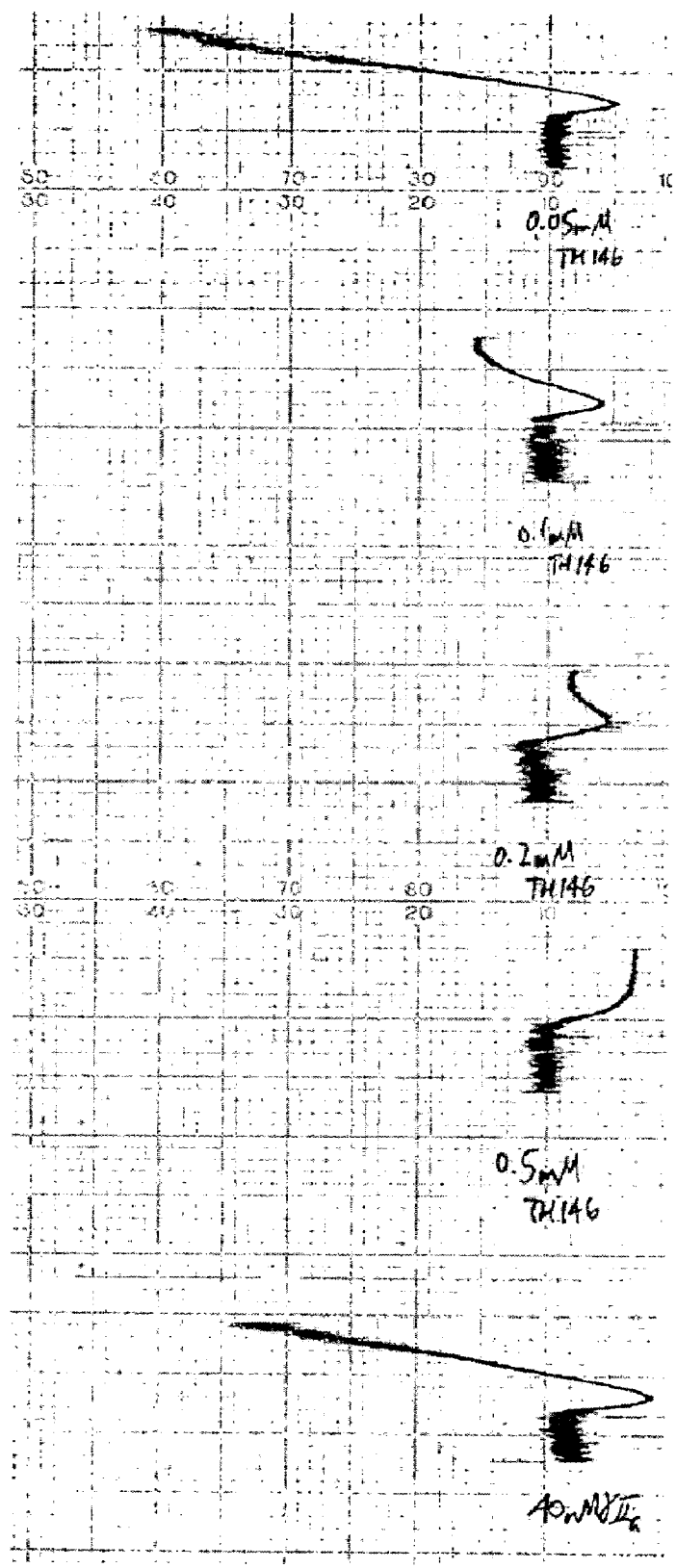
FIG. 1 illustrates the effect of the peptide rOicPGF (D-Arg-Oic-Pro-Gly-Phe) on γ-thrombin-induced platelet aggregation in human platelet-rich plasma. The figure shows aggregation tracings. In this representative experiment, 40 nM γ-thrombin was necessary to induce threshold platelet aggregation. When the platelets were pre-incubated with 0.5 mM rOicPGF (TH146) (D-Arg-Oic-Pro-Gly-Phe), there was complete inhibition of 40 nM γ-thrombin-induced platelet aggregation. At 0.1 mM rOicPGF (TH146) (D-Arg-Oic-Pro-Gly-Phe) there was a little recovery of platelet aggregation. At 0.05 mM rOicPGF (TH146) (D-Arg-Oic-Pro-Gly-Phe), there was full recovery of 40 nM γ-thrombin-induced platelet aggregation.
Figure 2:
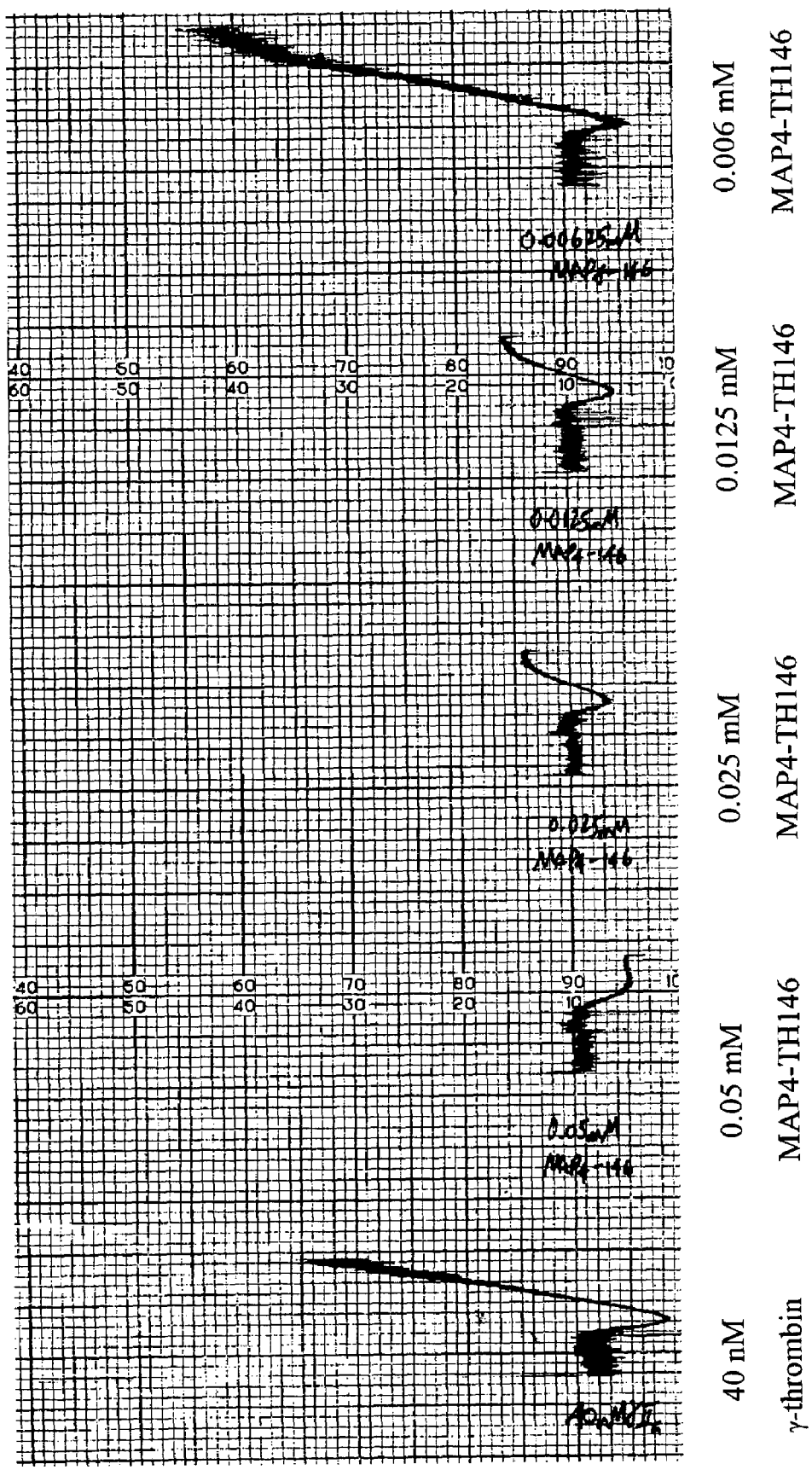
FIG. 2 illustrates the effect of MAP4-TH146 (MAP4-rOicPGF; γ-Ala-Lys-2Lys-4(-D-Arg-Oic-Pro-Gly-Phe)) on 40 nM γ-thrombin-induced platelet aggregation in human platelet-rich plasma. 0.05 mM MAP4-TH146 completely abolished 40 nM γ-thrombin-induced platelet aggregation. When the concentration of MAP4-TH146 was lowered to 0.006 mM, 40 nM γ-thrombin-induced platelet aggregation returned to pretreatment levels.

As shown in FIG. 1, 70 nM γ-thrombin induced a full platelet aggregatory response. The aggregation response was abolished by greater than or equal to 0.5 mM rOicPGF. At 0.25 mM rOicPGF, γ-thrombin-induced platelet aggregation returned to normal. In FIG. 2, 0.0125 mM or greater MAP4-TH146 (β-Ala-Lys-2Lys-4(D-Arg-Oic-Pro-Gly-Phe)) abolished 40 nM γ-thrombin-induced platelet aggregation. The most potent to least potent inhibitors of γ-thrombin-induced platelet aggregation are MAP4-rOicPGF, rOicPGF, rOicPGIdg, rOicHypGThi, rOicHypGIdg, rOicPGThi, rOicOicGIdg, rOicOicGThi, rIdgTicGF, rOicOicGF, and rOicHypGF, respectively, in decreasing order.

2. Calcium Mobilization Assay

Figure 3:
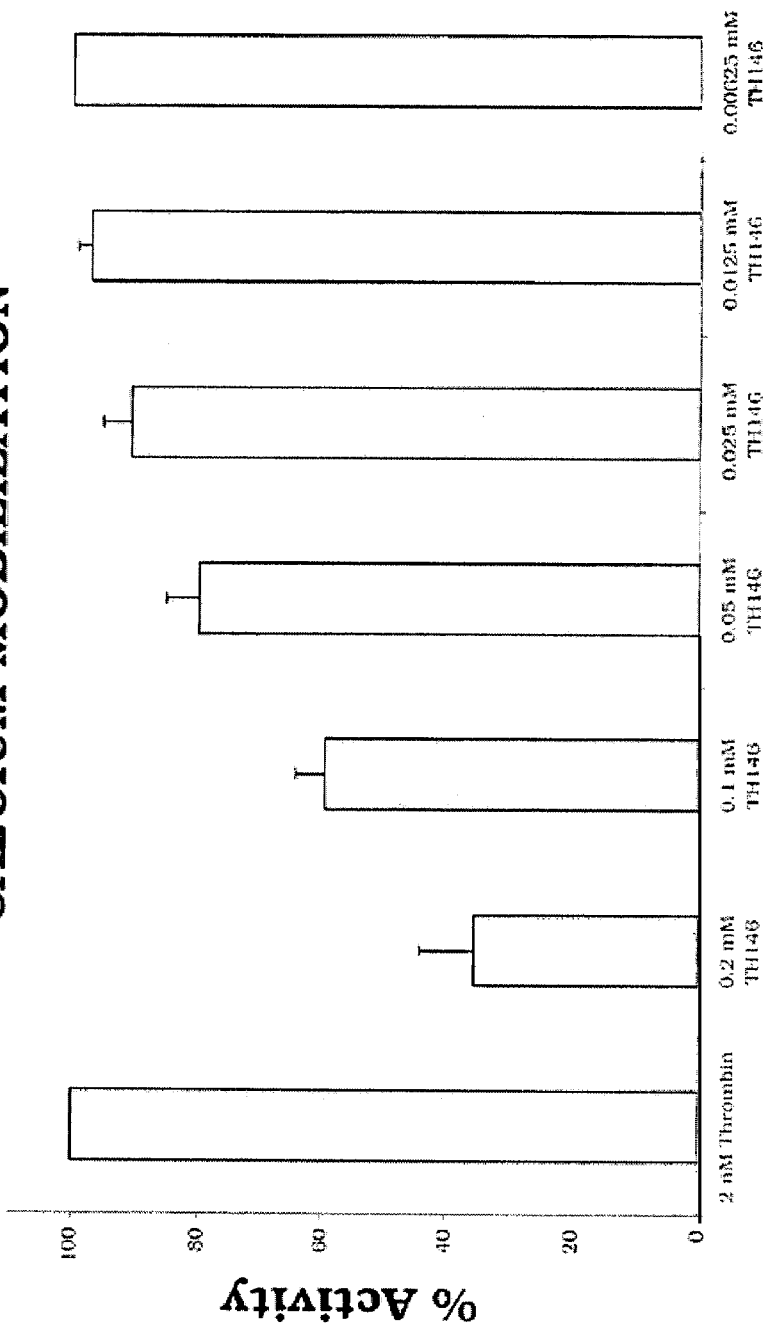
FIG. 3 illustrates the effect of the peptide rOicPGF (D-Arg-Oic-Pro-Gly-Phe) on α-thrombin-induced calcium mobilization in normal human lung fibroblasts. Two nM alpha thrombin was able to stimulate maximal calcium flux. When 0.2 mM rOicPGF was present, there was 63% inhibition of calcium mobilization. As the concentration of rOicPGF was decreased from 0.2 mM to 0.0125 mM, there was decreased inhibition of thrombin-induced calcium mobilization. At 0.00625 mM rOicPGF, there was full recovery of alpha thrombin-induced calcium mobilization.
Figure 4:
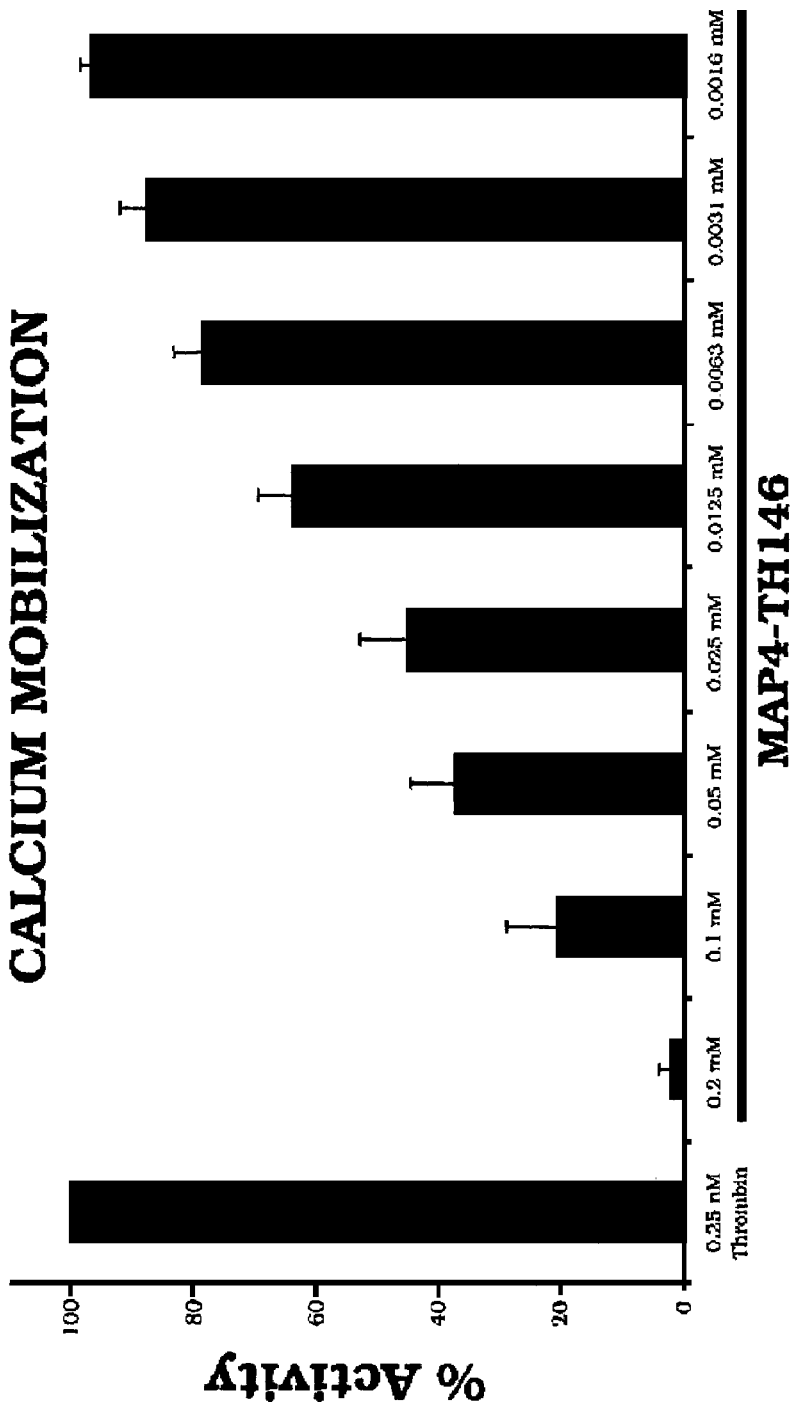
FIG. 4 illustrates the effect of MAP4-TH146 (MAP4-rOicPGF; β-Ala-Lys-2Lys-4(D-Arg-Oic-Pro-Gly-Phe)) on α-thrombin-induced calcium mobilization in normal human lung fibroblasts. Two nM alpha thrombin was able to stimulate maximal calcium flux. When 0.2 mM MAP4-TH146 was present, there was 98% inhibition of calcium mobilization. As the concentration of MAP4-TH146 was decreased from 0.2 mM to 0.0031 mM, there was decreased inhibition of thrombin-induced calcium mobilization. At 0.0016 MAP4-TH146, there was full recovery of alpha thrombin-induced calcium mobilization.

The second assay developed to assess peptides from the combinatorial libraries uses inhibition of α-thrombin-induced calcium mobilization in fibroblasts. Normal human lung fibroblasts (NHLF) were purchased from Clonetics, San Diego, Calif., an affiliate of Bio-Wittaker, Walkersville, Md. The cytoplasmic free $Ca^{2+}$ concentration ($[Ca^{2+}]_i$) was measured using the fluorescent $Ca^{2+}$ indicator fura-2 (Molecular Probes, Inc., Eugene, Oreg.). Suspension of fibroblasts in Hepes-Tyrode's buffer were loaded with fura-2 by incubation at 37° C. with 2 μM fura-2/acetoxymethyl ester for 45 minutes according to the method of Rasmussen et al., *J. Biol. Chem.* 268, 14322 (1993). The labeled fibroblasts were separated from excess probe by washing by centrifugation at 1000 rpm (180×g). Aliquots of the labeled fibroblasts were transferred into a quartz cuvette with a magnetic stirrer, which was then placed in a thermostatically controlled chamber at 37° C. in a fluorescence spectrophotometer (Perkin-Elmer LS50B spectrofluorometer, Chicago, Ill.). Reagents, test peptide, and α-thrombin (0.25–2 nM), were sequentially added directly to the cuvette. The excitation wavelengths varied between 340 and 380 nm. Fluorescence was measured by recording emitted light at 510 nm as reported by Fisher et al., *Mol Pharm.* 35, 195 (1989). The minimum emission was determined on a solubilized fibroblast sample in the presence of 10 mM EDTA; maximum emission was determined on the same sample with 10 mM $Ca^{2+}$ added. The intrafibroblast free $Ca^{2+}$ concentration was calculated by the method of Grykiewicz et al., *J. Biol. Chem.* 260, 3440 (1985). The ratio of the fluorescence readings was calculated as R=340/380 nm and processed according to the equation $[Ca^{2+}]_i = K_D((R-R_{min})/R_{max}-R))(S_{f2}/S_{b2})$ to determine the intrafibroblast free $Ca^{2+}$ concentration. The $K_D$ for fura-2 was assumed to be 224 nM. $R_{max}$ and $R_{min}$ are the maximum and minimum fluorescence ratios measured at the end of the experiment, respectively; $S_{f2}$ and $S_{b2}$ are the fluorescence values at 380 nm in the absence and presence of saturating $[Ca^{2+}]$, respectively. The reaction was monitored for 3–5 minutes. As shown in FIG. 3, peptide rOicPGF (D-Arg-Oic-Pro-Gly-Phe) blocked 0.25 nM α-thrombin-induced $Ca^{2+}$ mobilization in fibroblasts at concentrations ≧25 μM. As shown in FIG. 4, peptide MAP4-rOicPGF (β-Ala-Lys-2Lys-4(D-Arg-Oic-Pro-Gly-Phe)) blocked 0.25 nM α-thrombin-induced $Ca^{2+}$ mobilization in fibroblasts at concentrations ≧3.1 μM. Table II lists all the peptides from the most potent to the least potent inhibitor of thrombin-induced $Ca^{2+}$ mobilization. The table shows, in decreasing potency, the percent inhibition of thrombin-induced calcium mobilization using 0.1 mM of each of the peptides. The 11 most potent inhibitors in decreasing order were MAP4-rOicPGF, rOicPGF, rOicPGIdg, rOicHypGThi, rOicHypGIdg, rOicPGThi, rOicOicGIdg, rOicOicGThi, rIdgTicGF, rOicOicGF, and rOicHypGF, respectively.

3. Inhibition of Clot-based Coagulant Assays

Figure 5:
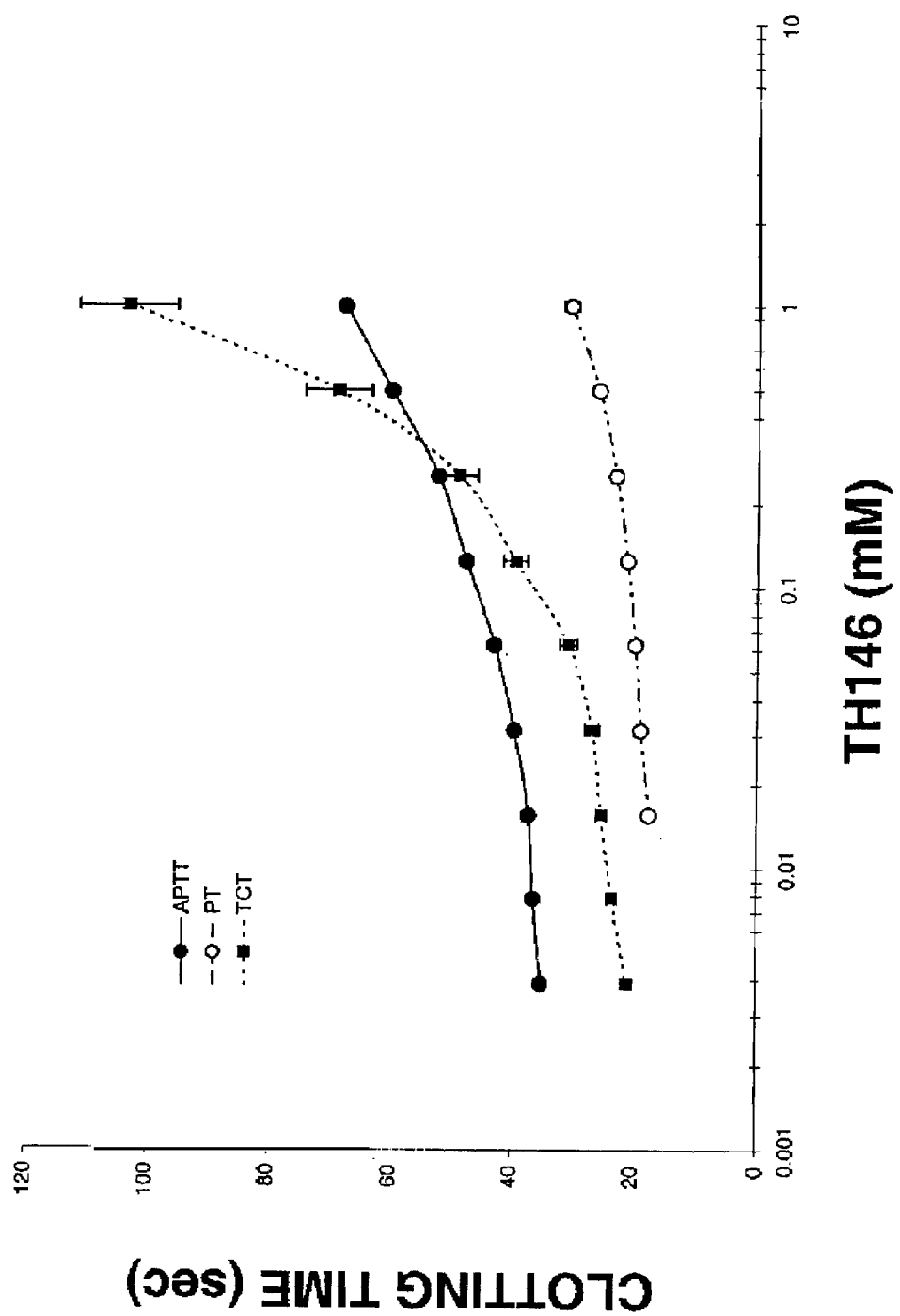
FIG. 5 illustrates the effect peptide rOicPGF (D-Arg-Oic-Pro-Gly-Phe) on the clotting time of normal human plasma using the activated partial thromboplastin time (APTT), prothrombin time (PT), or thrombin clotting time (TCT). At 3.7 μM, 30 μM, or 3.7 μM peptide rOicPGF, there was a significant prolongation of the APTT, PT, or TCT, respectively. These data indicate that peptide rOicPGF has a significant effect of directly interacting with α-thrombin itself.
Figure 6:
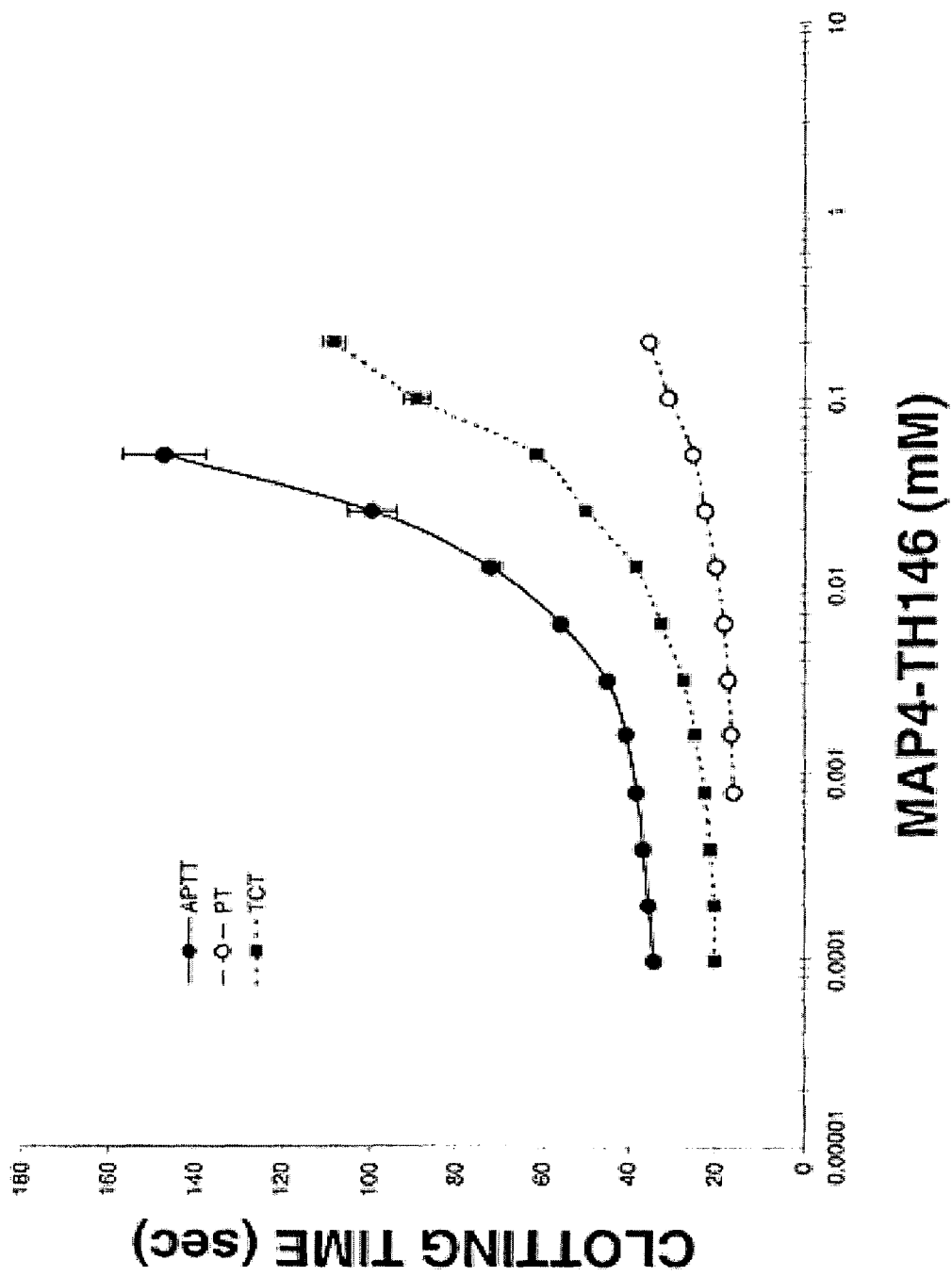
FIG. 6 illustrates the effect peptide MAP4-rOicPGF (β-Ala-Lys-2(Lys)-4(D-Arg-Oic-Pro-Gly-Phe)) on the clotting time of normal human plasma using the activated partial thromboplastin time (APTT), prothrombin time (PT), or thrombin clotting time (TCT). At 0.195 μM, 3.125 μM, or 0.39 μM peptide MAP4-rOicPGF, there was a significant prolongation (p<0.05) of the APTT, PT, or TCT, respectively. These data indicate that peptide MAP4-rOicPGF has a significant effect of directly interacting with α-thrombin itself.

The influence of the various peptide formulations used in the present invention on established coagulation-based assays was determined. The activated partial thromboplastin time (APTT) is performed by mixing 0.05 ml normal human citrated plasma with 0.05 ml activated partial thromboplastin reagent purchased from Organon Teknika, Research Triangle Park, N.C. in the absence or presence of a peptide inhibitor. After incubation for 5 min at 37° C., the mixture is recalcified with 0.05 ml of 30 mM calcium chloride and the time to clot formation is measured in an Amelung KC4A instrument (Sigma Chemical Corp, St. Louis, Mo.) (Hasan et al. *Thrombosis and Haemostasis.* 82, 1182–1187 (1999)). The prothrombin time (PT) is performed by mixing 0.05 ml normal human citrated plasma with 0.05 ml Simplastin (Organon Teknika, Research Triangle Park, N.C.) followed by incubation for 3 min at 37° C. in the absence or presence of a peptide inhibitor. At the addition of 0.05 ml of 30 mM calcium chloride, the time to clot formation is measured in an KC4A instrument (Sigma Chemical Corp, St. Louis, Mo.) (Hasan et al. *Thrombosis and Haemostasis.* 82, 1182–1187 (1999)). The thrombin clotting time (TCT) is performed by adding 0.1 ml normal human citrated plasma in the absence or presence of a peptide inhibitor and 0.05 ml of a α-thrombin solution such that the final concentration of the thrombin in the entire mixture was 1 nM. Upon addition of the thrombin, the time to clot formation is measured in an KC4A instrument (Sigma Chemical Corp, St. Louis, Mo.). In FIG. 5, peptide TH146 produces a significant prolongation ($p<0.05$) of the activated partial thromboplastin time at 15 μM, of the prothrombin time at 60 μM, and the thrombin clotting time at 15 μM. In FIG. 6, peptide MAP4-TH146 produced a significant prolongation ($p<0.05$) of the activated partial thromboplastin time at 0.195 μM, of the prothrombin time at 3.125 μM, and the thrombin clotting time at 0.39 μM.

4. Inhibition of RPPGF-biotin Binding to $rPAR1_{EC}$ by Various Peptides or Wild Type or Mutagenized $rPAR1_{EC}$ A recombinant form of the extracellular domain of human PAR1 was prepared. A portion of the extracellular domain of human PAR1 ($Ala^{26}$-$Ser^{99}$) ($rPAR1_{EC}$) was expressed in *Escherichia coli* using Novagen's bacterial expression system and its pET19b vector. Oligonucleotides primers for PCR were designed to place NdeI and XhoI restriction sites at the 5' and 3' ends of the coding sequence, respectively. Polymerase chain reaction (PCR) using human PAR1 cDNA as template prepared hPAR1 DNA encoding residues $Ala^{26}$-$Ser^{99}$. The NdeI-XhoI PCR fragment was ligated to the NdeI/XhoI sites of pET19b to create $pET19b/PAR1_{EC}$. This plasmid was then used to transform NovaBlue, an *E. coli* K12 strain. The insert of the cloned DNA was sequenced and it showed 100% fidelity with the DNA sequence of the targeted N-terminal extracellular domain of PAR1. The $His_{10}$-DDDDK-$PAR1_{EC}$ fusion construct was produced in *E. coli* strain BL21(DE3) (Novagen, Inc., Madison, Wis.) by transforming with $pET19b/PAR1_{EC}$ and inducing it with 1 mM IPTG for 2 h (isopropyl-β-D-thiogalactopyranoside). The expressed $rPAR1_{EC}$ ($Ala^{26}$-$Ser^{99}$) fusion protein was purified from bacterial cytosolic fractions by nickel-chelate affinity chromatography (HisTrap™ Affinity Column, Amersham Pharmacia Biotech, Inc., Piscataway, N.J.). The bound recombinant was eluted with 20 mM phosphate, 0.5 M NaCl, 500 mM imidazole, pH 7.4 and dialyzed into 0.01 M Tris, 0.15 M NaCl, pH 8 and stored in aliquots at −70° C. Recombinant $PAR1_{EC}$ was characterized by 16.5% tristricine sodium dodecyl sulfate polyacrylamide gel electrophoresis (SDS-PAGE), amino-terminal sequencing and immunoblotting with anti-PAR1 antibodies which consist of a polyclonal antibody in goats and a monoclonal antibody both raised to the peptide Asn-Ala-Thr-Leu-Asp-Pro-Arg-Ser-Phe-Leu-Leu-Arg (SEQ ID NO:3).

Deletion mutants of $rPAR1_{EC}$ also are prepared as follows. The $pET19b/PAR1_{EC}$ plasmid is used to express several deletion mutants (Mutants IV, V, and VII) of $rPAR1_{EC}$. Oligonucleotide-directed mutagenesis using GeneEditor mutagenesis kit (Promega, Madison, Wis.) was performed to generate the mutants $rPAR1_{EC}$ in the expression vector $pET19b/PAR1_{EC}$. Mutants are selected based upon the incorporation of a second-site mutation in β-lactamase, which alters its substrate specificity allowing resistance in transformed bacteria to cefotaxime and ceftriaxone in addition to ampicillin. Incorporation of the deletion was verified by DNA sequencing. The mutagenesis primers for introduction of site-directed deletion were as follows: Mutant IV primer, 5'-GCAACA AATGCCACCT-CATTTCTTCTCAGG-3' (SEQ ID NO:17); Mutant V primer, 5'-AATGCCACCTTAGATCTTCTCAGGAAC-CCC-3'(SEQ ID NO:18); and Mutant VII primer, 5'-AC-CCCCAATGATAAAGAGGATGAGGAGAAAAATG-3' (SEQ ID NO:19). Plasmid DNA was prepared using reagents supplied by Qiagen (Valencia, Calif.) and recombinant site-directed deletion mutants of the extracellular domain of human PAR1 were expressed in *E. coli* strain BL21(DE3) after induction with 1 mM IPTG. The expressed mutant proteins were purified from bacterial cytosol by nickel-chelate affinity chromatography as described above.

Figure 7:
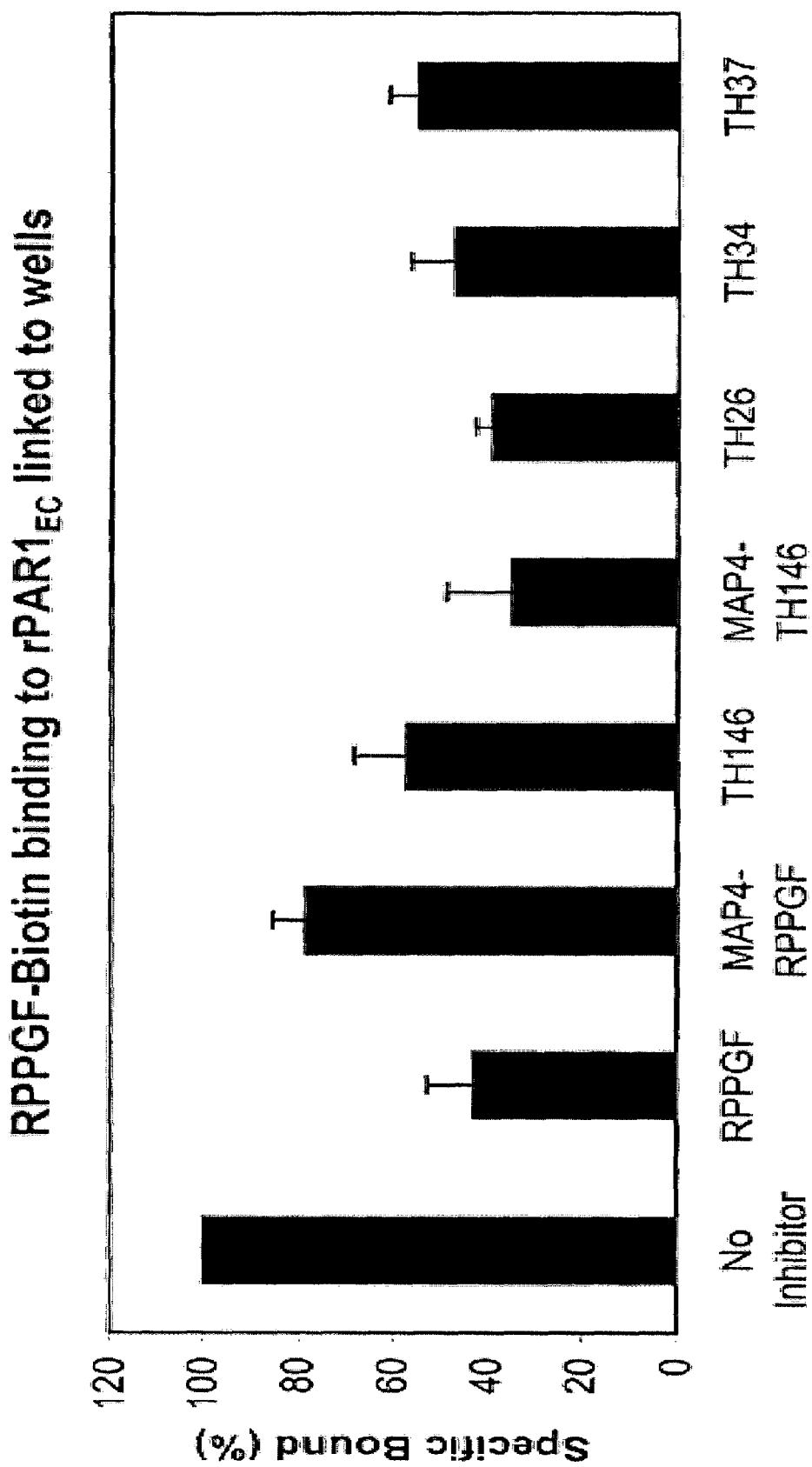
FIG. 7 illustrates the effect of various peptides on 50 μM RPPGF-biotin (Arg-Pro-Pro-Gly-Phe-biotin, SEQ ID NO:13) binding to recombinant protease activated receptor 1 extracellular domain ($rPAR1_{EC}$) bound to microtiter plate cuvette wells. In these experiments, the presence of 5 mM RPPGF (SEQ ID NO:4), MAP4-RPPGF ((β-Ala-Lys-2

The interaction of RPPGF-biotin (Arg-Pro-Pro-Gly-Phe-biotin, SEQ ID NO:13) with $rPAR1_{EC}$ is performed as follows: $rPAR1_{EC}$ is linked to microtiter plate cuvette wells at 1 μg/well on 0.1 M $Na_2CO_3$, pH 9.6 by overnight incubation at 4° C. After linking $rPAR1_{EC}$, 10 μM RPPGF-biotin (SEQ ID NO:13) was incubated in the cuvette wells in the absence or presence of increasing concentration of various peptides, 0.3 to 500 μM $rPAR1_{EC}$, Mutant IV, Mutant V, or Mutant VII $rPAR1_{EC}$. In FIG. 7, peptides MAP4-TH146 (β-Ala-Lys-2Lys-4(D-Arg-Oic-Pro-Gly-Phe), TH26, RPPGF (SEQ ID NO:4), TH34 (D-Arg-Oic-Pro-Gly-Idg), TH37 (D-Arg-Oic-Hyp-Gly-Thi), TH146 (D-Arg-Oic-Pro-Gly-Phe), or MAP4-RPPGF (β-Ala-Lys-2Lys-4(Arg-Pro-Pro-Gly-Phe)) in decreasing order blocked RPPGF-biotin (SEQ ID NO:13) binding to $rPAR1_{EC}$ bound to the microtiter plate. In FIG. 8, mutant forms of $rPAR1_{EC}$ that lacked the peptide sequence LDPR (Leu-Asp-Pro-Arg, SEQ ID NO:20) (Mutant IV) or PRSF (SEQ ID NO:15) (Mutant V) lost its ability to block RPPGF-biotin (SEQ ID NO:13) binding to $rPAR1_{EC}$ bound to the microtiter plate. The inability to inhibit RPPGF-biotin (SEQ ID NO:13) binding to the cuvette well with Mutants IV and V characterizes its mechanism of action of this group of compounds.

5. Inhibition of Thrombin- or Thrombocytin-induced Cleavage of $rPAR1_{EC}$

In FIG. 9, RPPGF (SEQ ID NO:4) blocks thrombocytin cleavage of recombinant human PAR1 extracellular domain at a concentration (0.5–1 mM) below that necessary to directly inhibit the active site of human α-thrombin. Thrombocytin is a snake venom enzyme that activates platelets by cleaving PAR1 at the thrombin cleavage site (Santos et al., *FEBS Letters*. 18, 3570–3577 (2000)). In FIG. 9, MAP4-RPPGF also inhibits the cleavage of PAR1 at a concentration (0.2–0.5 mM) that does not block the proteolytic activity of thrombocytin, a snake venom enzyme that activates platelets by cleaving PAR after arginine[41] (Santos et al., *FEBS Letters*. 18, 3570–3577 (2000); Hasan et al. *Amer. J. Physiol Heart Circ. Physiol*, In Press, (2003)). The ability of MAP4-rOicPGF to block thrombocytin cleavage of $rPAR1_{EC}$ was performed as follows. One μg of $rPAR1_{EC}$ in 0.01 mM Tris-HCL, 0.2 M NaCl, pH 8.0 was incubated at 37° C. for 15 min or 45 min with 1 nM of α-thrombin or 0.5 μg/mL thrombocytin (16.7 nM), respectively, in the absence or presence of 0.025 to 1 mM MAP4-rOicPGF. The reaction mixture was separated on SDS-PAGE and stained with Coomassie Brilliant Blue. The cleaved gel images were scanned using the software Scion Image, ScionCorp, Frederick, Md. In FIG. 10, MAP4-rOicPGF blocks thrombocytin-induced cleavage of recombinant extracellular domain of human PAR1 at 0.2 mM, a concentration below that necessary to block the proteolytic activity of the enzyme. This combined information indicates that various compounds of the present invention bind to PAR1 to prevent thrombocytin, and, possibly, thrombin cleavage of this substrate.

6. Inhibition of SILPAPRGYPGQ-biotin Binding to RPPGC or RPPGF-Biotin Binding to $rPAR4_{EC}$ Investigations were performed to determine if the compounds in the present invention interact with human PAR4. In FIG. 11, RPPGC (SEQ ID NO:10) was bound to plastic microtiter plates, After washing, biotinylated-SILPAPR-GYPGQ (SEQ ID NO:14) was incubated with the cuvette wells in the absence or presence of 0.001 to 5 mM RPPGF (SEQ ID NO:4), TH146, TH26, SIL12 (SEQ ID NO:9), or a scrambled peptide of RPPGF, FPRPG (Phe-Pro-Arg-Pro-Gly, SEQ ID NO:21). Peptide SILPAPRGYPGQ (Ser-Ile-Leu-Pro-Ala-Pro-Arg-Gly-Tyr-Pro-Gly-Gln, SEQ ID NO:9) is the thrombin binding and cleaving region on human PAR4. RPPGF (SEQ ID NO:4) and related peptide compounds blocked biotinylated- SILPAPRGYPGQ (SEQ ID NO:14) from binding to RPPGC (SEQ ID NO:4) linked to the cuvette well. These data indicate that the invention in this application interacts with the thrombin binding and cleaving sequence of human PAR4.

The extracellular fragment of human PAR4 has been expressed in bacteria. Human erythroleukemia (HEL) cells were used as a source for PAR4 mRNA. The level of PAR4 mRNA was substantially higher in HEL cells than washed human platelets. The sense primer for PCR (5'-GAATTC-CATATGGGCGGCACCCAGACCCCCAGCGTC-3', SEQ ID NO:22) had a Nde I restriction site and the antisense primer (5'-CCGCTCGAGTC-ACCTGGTGGGCAC-CCAGCCCAGAAG-3', SEQ ID NO:23) has a Xho I site for cloning into the Novagen pET19b vector to prepare pET19b-PAR4. These primers give a 204 basepair fragment which code for a 61 amino acid hPAR4 protein starting with Gly[18], the first amino acid after the signal peptide is removed, and finishing with Arg[78], the last amino acid of the extracellular fragment (Xu et al. *Proc. Natl. Acad. Sci*. 95, 6642–6646 (1998)). The pET19b-PAR4 vector after cloning was used to transform BL21 cells to express the recombinant protein. The expressed recombinant protein was purified on a DEAE Sephadex followed by a nickel affinity column (the recombinant protein has a 10 His-tag on its amino terminal end). The isolated, recombinant extracellular domain of PAR4 ($rPAR_{EC}$) is about 15 kDa on 16.5% Tris-Tricine SDS-PAGE. The recombinant protein is recognized as being human PAR4 by detection with an antibody prepared from a peptide ($S^{41}ILPAPRGYPGQ^{52}$) (SEQ ID NO:9) from human $PAR4_{EC}$. Recombinant $PAR4_{EC}$ was linked to microtiter plate cuvette wells. Goat polyclonal antibody to human PAR1, PAR3, or PAR4 was incubated with the coated microtiter plate cuvette wells and antibody binding was detected. Only antibody to PAR4 detected $rPAR4_{EC}$ linked to the microtiter plate wells. In FIG. 12, investigations showed that RPPGF (SEQ ID NO:4) or TH146 (D-Arg-Oic-Pro-Gly-Phe) at 5 mM block RPPGF-biotin (SEQ ID NO:13) (50 μM) from binding to $rPAR^4_{EC}$ that had been previous bound in 1 μg in 0.01 M $Na_2CO_3$, pH 9.6 to plastic microtiter plates. These studies indicate that peptides of the present invention also physically interact with human PAR4.

7. Inhibition of Thrombin-induced Motility of Prostate Cancer Cells

Motility assays are performed with a modified Boyden chamber (tissue culture-treated, 6.5 mm diameter, 10 μm thickness, 8 μm pores). In the motility assays, $2.5 \times 10^4$ cells are plated in the top chamber of non-coated polyethylene teraphthalate (PET) membranes (24-well insert, pore size 8 mm; Becton Dickinson). In motility and invasion assays, all cells are plated in serum free RPMI in the presence or absence of 1 nM α-thrombin and in the presence or absence of TH146 or MAP4-TH146. RPMI 10% fetal bovine serum is used as a chemoattractant in the lower chamber. The cells are incubated for 24 h and those that do not migrate through the pores in the membrane are removed by scraping the membrane with a cotton swab. The cells that transverse the membranes are stained with Dip-Quick (Jorgensen Laboratories, Loveland, Colo.). Cells in five random fields of view at 200× are counted and expressed as the average number of cells/field of view. The data are normalized to the number of cells that migrated in the absence of thrombin (0%) and in the presence of 1 nM thrombin (100%).

B. Clinical Indications for the Present Invention

The present invention is intended for use in individuals with acute coronary syndromes (crescendo angina, myocardial infarction) and in individuals who have acute coronary syndromes and receive percutaneous transluminal coronary angioplasty (PTCA) with an artificial stent placement. The present invention can be used as a single agent alone or in combinations with other agents. These other agents may include any one or number of the following drugs (including all of them): standard heparin, low molecular weight heparin, aspirin, ticlopidine, clopidogrel, abeiximab, tirofiban, or eptifibatide. The compounds of the present invention may be administered intravenously with the other agent(s) to treat individuals for acute coronary syndromes and during the related management. This invention also could be useful in the management of individuals with dacron grafts from peripheral bypass surgery and individuals with stents for carotid or renal artery stenosis. Agents such as those being presented here may be useful in the management of patients with transient ischemic attacks, stroke in progression, and complete stroke in the brain.

Purified peptides of the invention may be administered under circumstances where inhibition of thrombin-induced platelet activation or platelet aggregation is sought. The analogs are for use and administration to subjects experiencing platelet thrombosis from any cause, and may be used prophylactically in surgery or catheterization for insertion of artificial dacron grafts and stents to prevent reocclusion events due to platelet thrombi. Thus, the analogs may be infused into individuals to prevent strokes and cerebral edema. The biologic targets of this invention, human PAR1 and PAR4, may also be expressed on cells other than platelets and vascular endothelial cells. It is possible that they are expressed on cancer cells (Chay et al. *Urology* 60, 760–765 (2002)). Thus the compounds in the present invention may have use to prevent PAR1 or PAR4 activation in cancer cells and may be used to inhibit their motility. Further, the compounds of the present invention may be useful to interfere with other thrombin and/or PAR1 mediated activity. The compounds could be used to decrease thrombin-mediated brain edema (Jiang et al. *J Cerebral Blood Flow & Metabolism*. 22, 404–410 (2002)).

The analogs may be administered by any convenient means, which will result in substantial delivery into the blood stream. Preferably the administration is parenterally. However, the administration of analogs can be executed by any means which will introduce the analogs into the bloodstream, including intravenous or intranasal administration, as well as administration via a dermal patch or rectal suppositories. Intravenous administration is presently contemplated as the preferred administration route, although intranasal administration may also be utilized. Last, the nature of the compounds in the present invention is such that they contain D and synthetic amino acids which are less biodegradable than peptides consisting of L amino acids. Therefore, oral delivery mechanisms may be developed for these compounds as well.

The peptide analogs may be combined with any pharmaceutical carrier, which is physiologically acceptable to the host. The pharmaceutical composition may be compounded according to conventional pharmaceutical techniques. The carrier may be provided in a variety of forms depending on the form of preparation desired for administration. For parenteral administration, the carrier can comprise sterile water, and optionally other ingredients to aid solubility or preservative purposes. In intravenous administration, the preferred parenteral route, the analogs may be dissolved in appropriate intravenous delivery vehicles containing physiologically compatible substances, such as sterile sodium chloride having a buffered pH compatible with physiologic conditions, e.g. saline. Injectable suspension may also be prepared, in which case appropriate liquid carriers, suspending agents and the like may be employed.

The dosage of administration will depend on the size and weight of the patient. Those skilled in the art of infusion therapy in ICU or in interventional cardiology can derive appropriate dosages and schedules of administration to suit the specific circumstances and needs of the patient. The physiologically acceptable dosages range from about 10 to 30 mg per day per kg of body weight. In preferred intravenous administration, the dosage is 10 mg/kg body weight in 5 ml of normal saline or in any suitable vehicle given at a rate of 1 ml/min. The therapeutically optimal amounts of dosage may be determined by monitoring pre- and post-infusion platelet function by determining ex vivo γ-thrombin induced platelet aggregation and secretion, and also by measuring hemostatic parameters like activated partial thromboplastin time (APTT), prothrombin time (PT), thrombin clotting time (TCT), and template bleeding time (BT).

We claim:

1. A compound consisting of an amino acid sequence of formula $$A_1\text{-}A_2\text{-}A_3\text{-}A_4\text{-}A_5$$

wherein
- $A_1$ is selected from the group consisting of D-arginine (r) and L-arginine (R);
- $A_2$ is selected from the group consisting of (2S, 3aS, 7aS)-octahydroindole-2-carboxlic acid (Oic), Hydroxyproline (Hyp), α-(2-indanyl)glycine (Idg), proline (P), 1,2,3,4-tetrahydroisoquinoline-3-carboxylic acid (Tic), Pentafluorophenylalanine (F5F) and β-(2-thienyl)-L-alanine (Thi);
- $A_3$ is selected from the group consisting of Oic, Hyp, Idg, P, Tic, F5F, and Thi;
- $A_4$ is glycine (G);
- $A_5$ is selected from the group consisting of L-phenylalanine (F), Oic, Hyp, Idg, Tic, F5F and Thi;
- wherein at least one of $A_1$-$A_5$ is not a naturally occurring amino acid residue and wherein said compound is an inhibitor of at least one thrombin-mediated activity.

2. The compound of claim 1 wherein the activity is selected from the group consisting of thrombin-induced platelet aggregation, thrombin-induced calcium mobilization, thrombin-mediated coagulation, thrombin-induced cell motility and thrombin-induced cell adhesion.

3. The compound of claim 2 wherein the activity is thrombin-induced platelet aggregation.

4. The compound of claim 2 wherein the activity is thrombin-induced calcium mobilization.

5. The compound of claim 2 wherein the activity is thombin-mediated coagulation.

6. The compound of claim 3 that is an inhibitor of thrombin-induced calcium mobilization.

7. The compound of claim 3 that is an inhibitor of thrombin-mediated coagulation.

8. The compound of claim 2 wherein the activity is thrombin-induced cell motility.

9. The compound of claim 2 wherein the activity is thrombin-induced cell adhesion.

10. A compound selected from the group consisting of rOicPGF (D-Arg-Oic-Pro-Gly-Phe), rOicPGIdg (D-Arg-Oic-Pro-Gly-Idg), rOicHypGThi (D-Arg-Oic-Hyp-Gly-Thi), rOicHypGIdg (D-Arg-Oic-Hyp-Gly-Idg), rOicPGThi (D-Arg-Oic-Pro-Gly-Thi), rOicOicGIdg (D-Arg-Oic-Oic-Gly-Idg), rOicOicGThi (D-Arg-Oic-Oic-Gly-Thi), rIdgTicGF (D-Arg-Idg-Tic-Gly-Phe), rOicOicGF (D-Arg-Oic-Oic-Gly-Phe), and rOicHypGF (D-Arg-Oic-Hyp-Gly-Phe).

11. A compound having the formula β-Ala-Lys-2Lys-4 ($A_1$-$A_2$-$A_3$-$A_4$-$A_5$)
wherein
- $A_1$ is selected from the group consisting of D-arginine (r) and L-arginine (R);
- $A_2$ is selected from the group consisting of (2S, 3aS, 7aS)-octahydroindole-2-carboxlic acid (Oic), Hydroxyproline (Hyp), α-(2-indanyl)glycine (Idg), proline (P), 1,2,3,4-tetrahydroisociuinoline-3-carboxylic acid (Tic), Pentafluorophenylalanine (F5F) and β-(2-thienyl)-L-alanine (Thi);
- $A_3$ is selected from the group consisting of Oic, Hyp, Idg, P, Tic, F5F, and Thi;

$A_4$ is glycine (G);

$A_5$ is selected from the group consisting of L-phenylalanine (F), Gic, Hyp, Idg, Tic, F5F and Thi;

wherein at least one of $A_1$-$A_5$ is not a naturally occurring amino acid residue and wherein said compound is an inhibitor of at least one thrombin-mediated activity.

12. A compound having the formula β-Ala-Lys-2Lys-4(D-Arg-Oic-Pro-Gly-Phe).

13. A method of inhibiting thrombin activation of mammalian cells having thrombin receptors, said method comprising contacting said cells with an effective amount of the compound of claim 11.

14. The method of claim 13 wherein said compound is β-Ala-Lys-2Lys-4(D-Arg-Oic-Pro-Gly-Phe).

15. A pharmaceutical composition comprising the compound of claim 1 and a physiologically acceptable carrier.

16. A pharmaceutical composition comprising the compound of claim 10 and a physiologically acceptable carrier.

17. A pharmaceutical composition comprising the compound of claim 11 and a physiologically acceptable carrier.

18. A pharmaceutical composition comprising the compound of claim 12 and a physiologically acceptable carrier.

* * * * *